US009539257B2

(12) United States Patent
Bing et al.

(10) Patent No.: US 9,539,257 B2
(45) Date of Patent: Jan. 10, 2017

(54) METHOD OF TREATING CANCER

(71) Applicant: NOVARTIS AG, Basel (CH)

(72) Inventors: Nan Bing, Research Triangle Park, NC (US); Linda Perry Briley, Research Triangle Park, NC (US); Laura R. Budde, Research Triangle Park, NC (US); Charles J. Cox, Stevenage (GB); Colin F. Spraggs, Stevenage (GB)

(73) Assignee: Novartis AG (CH)

( * ) Notice: Subject to any disclaimer, the term of this patent is extended or adjusted under 35 U.S.C. 154(b) by 0 days.

(21) Appl. No.: 14/634,052

(22) Filed: Feb. 27, 2015

(65) Prior Publication Data
US 2015/0231137 A1 Aug. 20, 2015

Related U.S. Application Data

(63) Continuation of application No. 13/391,579, filed as application No. PCT/US2010/046142 on Aug. 20, 2010, now abandoned.

(60) Provisional application No. 61/307,569, filed on Feb. 24, 2010, provisional application No. 61/235,947, filed on Aug. 21, 2009.

(51) Int. Cl.
*C12Q 1/68* (2006.01)
*A61K 31/517* (2006.01)
*A61K 39/00* (2006.01)
*A61K 31/7068* (2006.01)
*A61K 31/337* (2006.01)
*A61K 31/506* (2006.01)
*A61K 31/4196* (2006.01)

(52) U.S. Cl.
CPC .......... *A61K 31/517* (2013.01); *A61K 31/337* (2013.01); *A61K 31/4196* (2013.01); *A61K 31/506* (2013.01); *A61K 31/7068* (2013.01); *A61K 39/0011* (2013.01); *C12Q 1/6886* (2013.01); *C12Q 2600/106* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS

2007/0190583 A1 8/2007 Spector et al.
2007/0281041 A1 12/2007 Ramesh et al.
2008/0131887 A1 6/2008 Stephan et al.
2009/0192101 A1 7/2009 Hung et al.

FOREIGN PATENT DOCUMENTS

WO 2008112903 A2 9/2008

OTHER PUBLICATIONS

Chen et al Clin Chem Lab Med. 2007. 45(5):611-614.*
Liu et al., "Lapatinb", Chinese Journal of Medicinal Chemistry, 2007, vol. 17, No. 5, p. 333.
Moy et al., "Hepatobiliary abnormalities in patients with metastatic cancer treated with Lapatinib", Journal of Clinical Oncology, 2009 ASCO Annual Meeting Proceedings (Post-Meeting Edition), vol. 27, No. 15S, p. 1043, 2009.
O'Donohue et al., "Co-amoxiclav jaundice: clinical and histological feature and HLA class II association", Gut, 2000, vol. 47, No. 5, pp. 717-720.
Glaxosmithkline, "HLA-DQ*0201 is a major determinant of lapatinib-induced hepatotoxicity risk in women with advanced breast cancer", FDA/PhRMA/AASLD DILI Meeting, 2010.
Hirata et al., "Ticlopidine-induced hepatotoxicity is associated with specific human leukocyte antigen genomic subtypes in Japanese patients: a preliminary case-control study", The Pharmacogenomics Journal, 2008, vol. 8, pp. 29-33.
Zao GlaxoSmithKine Trading, Russia, Marketing Authorization of Tyverb, Lapatinib, 250 mg, State Register of the Medicines, Registration No. ICP-00078208, Feb. 15, 2008.
Starkova, "Clinical Endocrinology", Medical Guide, 1991, pp. 192, 202.
Strassburg et al., "Pharmacogenetics of Gilbert's syndrome", Pharmacogenomics, 2008, vol. 9, No. 6, pp. 703-715.
Corkery, et al., "Targeted treatment of advanced and metastatic breast cancer with lapatinib", OncoTargets and Therapy, vol. 1, pp. 21-34 (2008).
Roses, "Pharmacogenetics in drug discovery and development: a translational perspective", National Drug Discovery, 2008, vol. 7, pp. 807-817.
Zubillaga, et al., "HLA-DQA1 and HLA-DQB1 Genetic Markers and Clinical Presentation in Celiac Disease", Journal of Pediatric Gastroenterology and Nutrition, 2002, vol. 34, pp. 548-554.
West, "Malignancy and mortality in people with celiac disease: population based cohort study" BMJ, 2004, vol. 329, No. 7468; abstract.

* cited by examiner

Primary Examiner — Carla Myers
(74) Attorney, Agent, or Firm — Sandra Rueck

(57) ABSTRACT

Methods are provided of treating a human for cancer comprising administering at least one dose of lapatinib, or a pharmaceutically acceptable salt or composition thereof, to a patient, wherein said patient does not have one or more allelic polymorphisms selected from the group of: HLA-DQA1*0201, HLA-DQB1*0202, and HLADRB1*0701. Patients may also be free of genotypes in TNXB; rs12153855 and/or rs17207923.

6 Claims, 3 Drawing Sheets

METHOD OF TREATING CANCER

This application is a continuation of U.S. application Ser. No. 13/391,579, which claims priority to International Application No. PCT/US2010/046142, filed 20 Aug. 2010, each of which is incorporated herein by reference. This application also claims benefit of the filing date of U.S. Applications Nos. 61/235,947, filed 21 Aug. 2009, and No. 61/307,569, filed 24 Feb. 2010.

FIELD OF THE INVENTION

The invention relates to methods for treating cancer with lapatinib, or a pharmaceutically acceptable salt or composition thereof, genetic markers useful in such treatment, and methods and reagents for detecting such genetic markers.

BACKGROUND OF THE INVENTION

Liver signals, including alanine aminotransferase (ALT) and total bilirubin (TBL) are routinely monitored during clinical trials of new drugs and/or administration of marketed drugs for safety profiling. Hepatotoxicity can occur if a patient experiences ALT (>3x) and/or TBL (>2x) above the upper limits of normal (ULN). Pharmacogenetics may provide insights into mechanisms of hepatotoxicity.

Methods of treating patients with pharmacogenetic profiles that do not make them susceptible to hepatotoxicity with pharmaceutical compounds are needed.

SUMMARY OF THE INVENTION

Methods are provided for treating a human for cancer comprising administering at least one dose of lapatinib, or a pharmaceutically acceptable salt or composition thereof, to a human, wherein said human does not have one or more allelic polymorphisms selected from: HLA-DQA1*0201, HLA-DQB1*0202 and HLA-DRB1*0701.

DETAILED DESCRIPTION

Figure 1:
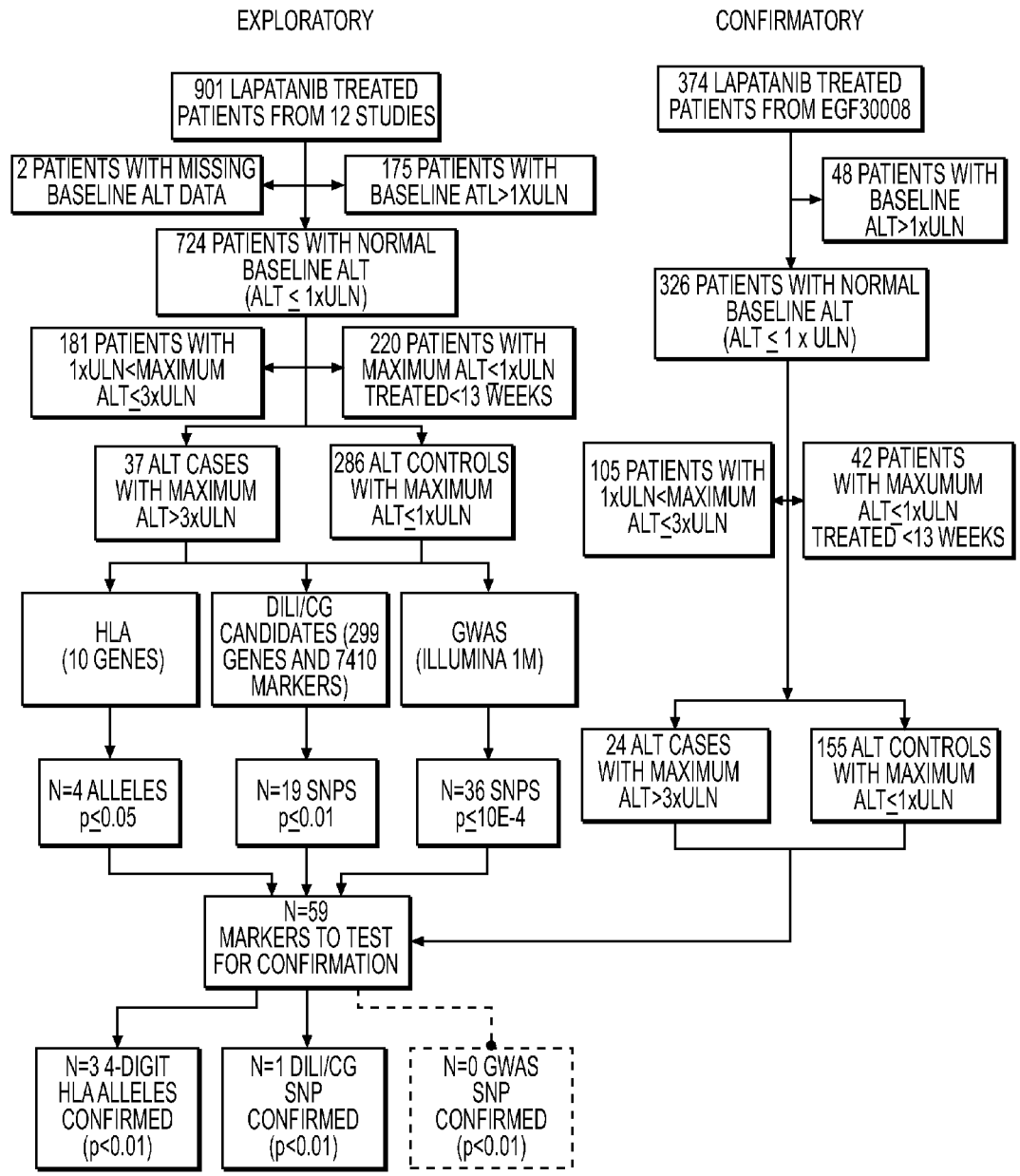
FIG. 1: Overall Study Design for two-stage analysis of exploratory marker association identification, followed by pre-specified marker confirmation in independent datasets using ALT case-control analysis.

Lapatinib is a tyrosine kinase inhibitor. Tyrosine kinase is associated with at least two oncogenes Epidermal Growth Factor Receptor (EGFR) and Human EGFR type 2 (Her2/neu). Overexpression of HER2/neu can be responsible for or correlated with certain types of high-risk breast cancers in women. Among other activities, lapatinib decreases tumor-causing breast cancer stem cells. One aspect of lapatinib's mechanism of action is that it inhibits receptor signal processes by binding to the ATP-binding pocket of the EGFR/HER2 protein kinase domain, preventing self-phosphorylation and subsequent activation of the signal mechanism.

Lapatinib is a small molecule and a member of the 4-anilinoquinazoline class of kinase inhibitors. In its currently marketed form, lapatinib is present as a monohydrate of the ditosylate salt, with chemical name N-(3 chloro-4-{[(3-fluorophenyl)methyl]oxy}phenyl)-6-[5-({[2 (methylsulfonyl)ethyl]amino}methyl)-2-furanyl]-4-quinazolinamine bis(4 methylbenzenesulfonate)monohydrate. It has the molecular formula $C_{29}H_{26}ClFN_4O_4S \cdot (C_7H_8O_3S)_2 \cdot H_2O$ and a molecular weight of 943.5 daltons. Lapatinib ditosylate monohydrate has the following chemical structure:

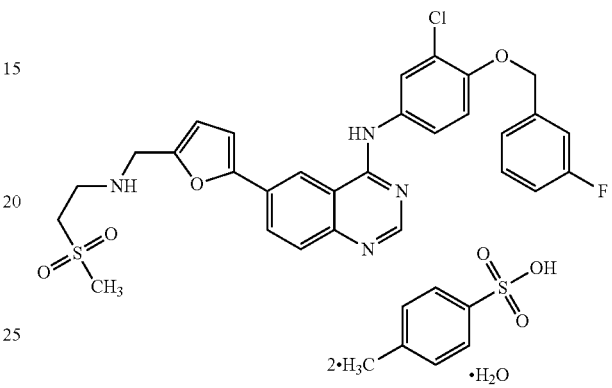

Lapatinib, pharmaceutically acceptable salt or compositions thereof, and compositions comprising lapatinib and uses are disclosed in, for example, U.S. Pat. Nos. 6,391,874, 6,828,320, 6,727,256, 6,713,485, and 7,157,466. Lapatinib is commercially available as TYKERB® and TYVERB®.

HLA

The HLA complex of humans (major histocompatibility complex or MHC) is a cluster of linked genes located on chromosome 6, which is also known as the MHC region. The HLA complex is classically divided into three regions: class I, II, and III regions (Klein J. In: Gotze D, ed. *The Major Histocompatibility System in Man and Animals*, New York: Springer-Verlag, 1976: 339-378). Class I HLAs comprise the transmembrane protein (heavy chain) and a molecule of beta-2 microglobulin. The class I transmembrane proteins are encoded by the HLA-A, HLA-B and HLA-C loci. A function of class I HLA molecules is to present antigenic peptides (including, for example, viral protein antigens) to T cells. Three isoforms of class II MHC molecules, denoted HLA-DR, -DQ, and -DP are currently recognized. The MHC class II molecules are heterodimers composed of an alpha chain and a beta chain; different alpha- and beta-chains are encoded by subsets of A genes and B genes, respectively. Various HLA-DR haplotypes have been recognized, and differ in the organization and number of DRB genes present on each DR haplotype; multiple DRB genes have been described. Bodmer et al., Eur. J. Immunogenetics 24:105 (1997); Andersson, Frontiers in Bioscience 3:739 (1998).

The MHC region exhibits high polymorphism; more than 1200 genotypical alleles of HLA-B have been reported. See e.g., Schreuder et al., *Human Immunology* 60: 1157-1181 (1999); Bodmer et al., *European Journal of Immunogenetics* 26: 81-116 (1999). Despite the number of alleles at the HLA-A, HLA-B and HLA-C loci, the number of haplotypes observed in populations is smaller than mathematically expected. Certain alleles tend to occur together on the same haplotype, rather than randomly segregating. This association is called linkage disequilibrium (LD) and may be quantitated by methods that are known in the art (see, e.g., Devlin and Risch, *Genomics* 29:311 (1995); BS Weir, Genetic Data Analysis II, Sinauer Associates, Sunderland, Md. (1996)).

The products encoded by the polymorphic HLA loci are commonly typed by serological methods for transplant and transfusion histocompatibility testing, and blood component therapy. Serological typing is based on reactions between characterized sera and the HLA gene products. Known techniques for histocompatibility testing include microlymphocytotoxicity and flow cytometry. Standard microlymphocytotoxicity for HLA antigen typing determines the HLA antigen profile of a subject's lymphocytes, using a panel of well characterized HLA antisera. Certain IILA alleles are well characterized, and serologic methods of detecting them are known. Sec e.g., *ASHI Laboratory Manual*, Fourth Edition, American Society for Histocompatibility and Immunogenetics (2000); Hurley et al., *Tissue Antigens* 50:401 (1997).

More recently, methods for analysis of HLA polymorphisms at the genetic level have been developed. Nonserological HLA typing methods include the use of DNA restriction fragment length polymorphism (RFLP; see e.g., Erlich U.S. Pat. No. 4,582,788 (1986)), or labelled oligonucleotides, to identify specific HLA DNA sequences. Such methods may detect polymorphisms located in either the coding or noncoding sequence of the genome. See e.g., Bidwell et al, *Immunology Today* 9:18 (1988), Angelini et al., *Proc. Natl. Acad. Sci. USA*, 83:4489 (1986); Scharf et al., *Science*, 233:1076 (1986); Cox et al., *Am. J. Hum. Gen.*, 43:954 (1988); Tiercy et al., *Proc. Natl. Acad. Sci. USA* 8.5:198 (1988); and Tiercy et aL, *Hum. Immunol.* 24:1 (1989). The polymerase chain reaction (PCR) process (see, e.g. U.S. Pat. No. 4,683,202, 1987) allows amplification of genomic DNA and may be used for HLA typing procedures. See, e.g. Saiki et al., *Nature* 324:163 (1986); Bugawan et al., *J. Immunol.* 141:4024 (1988); Gyllensten et al., *Proc. Natl. Acad. Sci. USA*, 85:7652 (1988). Scc also e.g., Ennis et al., *PNAS USA* 87:2833 (1990); Petersdorf et al., *Tissue Antigens* 46: 77 (1995); Girdlestone et al., *Nucleic Acids Research* 18:6702 (1990); Marcos et al., *Tissue Antigens* 50:665 (1997); Steiner et al., *Tissue Antigens* 57:481 (2001); Madrigal et al., *J. Immunology* 149:3411 (1992).

MICA and MICB

The MHC (HLA) class I chain-related gene A (MICA) and MHC (HLA) class I chain-related gene B (MICB) belong to a multicopy gene family located in the major histocompatibility complex (MHC) class I region near the HLA-B gene. They are located within a linkage region on chromosome 6p around HLA-B.

MICA is reported as highly polymorphic. The occurrence of MICA single nucleotide polymorphisms in various ethnic groups is reported by Powell et al., Mutation Research 432:47 (2001). Polymorphisms in MICA have been reported to be associated with various diseases, although in some cases the association was attributable to linkage disequilibrium with HLA genes. See, e.g., Salvarani et al., *J Rheumatol* 28:1867 (2001); Gonzalez et al., *Hum Immunol* 62:632 (2001); Seki et al., *Tissue Antigens* 58:71 (2001).

Various polymorphic forms of MICB have been reported (see, e.g., Visser et al., *Tissue Antigens* 51:649 (1998); Kimura et al., *Hum Immunol* 59:500 (1998); Ando et al., *Immunogenetics* 46:499 (1997); Fischer et al., *Eur J Immunogenet* 26:399 (1999)).

As is well known in Genetics, nucleotide and related amino acid sequences obtained from different sources for the same gene may vary both in the numbering scheme and in the precise sequence. Such differences may be due to numbering schemes, inherent sequence variability within the gene, and/or to sequencing errors. Accordingly, reference herein to a particular polymorphic site by number (e.g., HLA-DR) will be understood by those of skill in the art to include those polymorphic sites that correspond in sequence and location within the gene, even where different numbering/nomenclature schemes are used to describe them.

As used herein, a drug-induced "hepatotoxicity" refers to elevated ALT to greater than 3 times (>3× the Upper Limit of Normal (ULN)) either alone and/or with elevated Total Bilirubin (TBL) to greater than 2 times (>2×ULN) at the same time in the same human or other clinical features caused by liver injury.

As used herein "human," "human subject," "subject," and "patient" can be used interchangeably to mean any human.

Administering lapatinib, or a pharmaceutically acceptable salt or composition thereof, to a subject (or "treating" a subject with lapatinib) comprises methods and routes of administration as are known in the art. Recommended therapeutic regimes (dosing amounts and schedules, plasma concentrations) of lapatinib, and pharmaceutically acceptable salt or compositions thereof, are known in the art. As used herein, administration of lapatinib, or a pharmaceutically acceptable salt or composition thereof, is not limited to the treatment of breast cancer but includes its medical use for other conditions amenable to treatment with lapatinib, or pharmaceutically acceptable salt or compositions thereof.

As used herein, administration of a pharmaceutical kinase inhibitor to a subject comprises administration of an effective amount of the pharmaceutical agent to a subject in need thereof. The dose of a pharmaceutical agent can be determined according to methods known and accepted in the pharmaceutical arts, and can be determined by those skilled in the art.

As used herein, the "HLA allele" refers to one or more of the following alleles: IILA-DQA1*0201, IILA-DQB1*0202, IILA-DRB1*0701 and other markers in linkage disequilibrium with these alleles.

As used herein, "genotyping" a subject (or DNA or other biological sample) for a polymorphic allele of a gene(s) means detecting which allelic or polymorphic form(s) of the gene(s) or gene expression products (e.g., hnRNA, mRNA or protein) are present or absent in a subject (or a sample). Related RNA or protein expressed from such gene may also be used to detect polymorphic variation. As is well known in the art, an individual may be heterozygous or homozygous for a particular allele. More than two allelic forms may exist, thus, there may be more than three possible genotypes. For purposes of the present invention, "genotyping" includes the determination of HLA alleles using suitable serologic techniques, as are known in the art. As used herein, an allele may be 'detected' when other possible allelic variants have been ruled out; e.g., where a specified nucleic acid position is found to be neither adenine (A), thymine (T) or cytosine (C), it can be concluded that guanine (G) is present at that position (i.e., G is 'detected' or 'diagnosed' in a subject). Sequence variations may be detected directly (by, e.g, sequencing) or indirectly (e.g., by restriction fragment length polymorphism analysis, or detection of the hybridization of a probe of known sequence, or reference strand conformation polymorphism), or by using other known methods.

As used herein, a "genetic subset" of a population consists of those members of the population having a particular genotype. In the case of a biallelic polymorphism, a population can potentially be divided into three subsets: homozygous for allele 1 (1,1), heterozygous (1,2), and homozygous for allele 2 (2,2). A 'population' of subjects may be defined using various criteria, e.g., individuals being treated with lapatinib or individuals with cancer.

As used herein, a subject that is "predisposed to" or "at increased risk of" a particular phenotypic response based on genotyping will be more likely to display that phenotype than an individual with a different genotype at the target polymorphic locus (or loci). Where the phenotypic response is based on a multi-allelic polymorphism, or on the genotyping of more than one gene, the relative risk may differ among the multiple possible genotypes.

An allele refers to one specific form of a genetic sequence (such as a gene) within a cell, a sample, an individual or within a population, the specific form differing from other forms of the same gene in the sequence of at least one, and frequently more than one, variant sites within the sequence of the gene. The sequences at these variant sites that differ between different alleles are termed "variants", "polymorphisms", or "mutations." In general, polymorphism is used to refer to variants that have a frequency of at least 1% in a population, while the term mutation is generally used for variants that occur at a frequency of less than 1% in a population. In diploid organisms such as humans, at each autosomal specific chromosomal location or "locus" an individual possesses two alleles, a first inherited from one parent and a second inherited from the other parent, for example one from the mother and one from the father. An individual is "heterozygous" at a locus if it has two different alleles at the locus. An individual is "homozygous" at a locus if it has two identical alleles at that locus.

A polymorphism may comprise one or more base changes, an insertion, a repeat, or a deletion. A polymorphic locus may be as small as one base pair. Polymorphic markers include restriction fragment length polymorphisms, variable number of tandem repeats (VNTR's), hypervariable regions, minisatellites, dinucleotide repeats, trinucleotide repeats, tetranucleotide repeats, simple sequence repeats, and insertion elements such as Alu. The first identified allelic form is arbitrarily designated as the reference form and other allelic forms are designated as alternative or variant alleles. The allelic form occurring most frequently in a selected population is sometimes referred to as the wild type form. The most frequent allele may also be referred to as the major allele and the less frequent allele as the minor allele. Diploid organisms may be homozygous or heterozygous for allelic forms. A diallelic polymorphism has two forms. A triallelic polymorphism has three forms. A polymorphism between two nucleic acids can occur naturally, or be caused by exposure to or contact with chemicals, enzymes, or other agents, or exposure to agents that cause damage to nucleic acids, for example, ultraviolet radiation, mutagens or carcinogens.

Single nucleotide polymorphisms (SNPs) are positions at which two alternative bases occur at appreciable frequency (>1%) in the human population, and are the most common type of human genetic variation. Approximately 90% of all polymorphisms in the human genome are SNPs. SNPs are single base positions in DNA at which different alleles, or alternative nucleotides, exist in a population. An individual may be homozygous or heterozygous for an allele at each SNP position. A SNP can, in some instances, be referred to as a "cSNP" to denote that the nucleotide sequence containing the SNP is an amino acid coding sequence. As used herein, references to SNPs and SNP genotypes include individual SNPs and/or haplotypes, which are groups of SNPs that are generally inherited together. Haplotypes can have stronger correlations with diseases or other phenotypic effects compared with individual SNPs, and therefore may provide increased diagnostic accuracy in some cases (Stephens et al. Science 293, 489-493, 20 Jul. 2001).

Causative SNPs are those SNPs that produce alterations in gene expression or in the expression, structure, and/or function of a gene product, and therefore are most predictive of a possible clinical phenotype. One such class includes SNPs falling within regions of genes encoding a polypeptide product, i.e. cSNPs. These SNPs may result in an alteration of the amino acid sequence of the polypeptide product (i.e., non-synonymous codon changes) and give rise to the expression of a defective or other variant protein. Furthermore, in the case of nonsense mutations, a SNP may lead to premature termination of a polypeptide product. Causative SNPs do not necessarily have to occur in coding regions; causative SNPs can occur in, for example, any genetic region that can ultimately affect the expression, structure, and/or activity of the protein encoded by a nucleic acid. Such genetic regions include, for example, those involved in transcription, such as SNPs in transcription factor binding domains, SNPs in promoter regions, in areas involved in transcript processing, such as SNPs at intron-exon boundaries that may cause defective splicing, or SNPs in mRNA processing signal sequences such as polyadenylation signal regions. Some SNPs that are not causative SNPs nevertheless are in close association with, and therefore segregate with, a disease-causing sequence. In this situation, the presence of a SNP correlates with the presence of or predisposition to, or an increased risk in developing the disease. These SNPs, although not causative, are nonetheless also useful for diagnostics, disease predisposition screening, and other uses, such as, but not limited to, predicting hepatotoxicity as is described by the present invention.

An association study of a SNP and a specific disorder or a predisposition to a safety event involves determining the presence or frequency of the SNP allele in biological samples from individuals with the disorder or predisposition to a safety event of interest and comparing the information to that of controls (i.e., individuals who do not have the disorder or experience the same safety event).

A SNP may be screened in diseased tissue samples or any biological sample obtained from an individual, and compared to control samples, and selected for its increased (or decreased) occurrence in a specific pathological condition. Once a statistically significant association is established between one or more SNP(s) and a pathological condition (or other phenotype) of interest, then the region around the SNP can optionally be thoroughly screened to identify the causative genetic locus/sequence(s) (e.g., causative SNP/mutation, gene, regulatory region, etc.) that influences the pathological condition or phenotype.

Clinical trials have shown that patient response to treatment with pharmaceuticals is often heterogeneous. There is a continuing need to improve pharmaceutical agent design and therapy. In that regard, SNPs can be used to identify patients most suited to therapy with particular pharmaceutical agents (this is often termed "pharmacogenomics"). Similarly, SNPs can be used to exclude patients from certain treatment due to the patient's increased likelihood of developing toxic side effects or their likelihood of not responding to the treatment. Pharmacogenomics can also be used in pharmaceutical research to assist the drug development and selection process. (Linder et al. (1997), Clinical Chemistry, 43, 254; Marshall (1997), Nature Biotechnology, 15, 1249;

International Patent Application WO 97/40462, Spectra Biomedical; and Schafer et al. (1998), Nature Biotechnology, 16, 3).

Several techniques for the detection of mutations have evolved based on the principal of hybridization analysis. For example, in the primer extension assay, the DNA region spanning the nucleotide of interest is amplified by PCR, or any other suitable amplification technique. After amplification, a primer is hybridized to a target nucleic acid sequence, wherein the last nucleotide of the 3' end of the primer anneals immediately 5' to the nucleotide position on the target sequence that is to be analyzed. The annealed primer is extended by a single, labelled nucleotide triphosphate. The incorporated nucleotide is then detected.

The sequence of any nucleic acid including a gene or PCR product or a fragment or portion thereof may be sequenced by any method known in the art (e.g., chemical sequencing or enzymatic sequencing). "Chemical sequencing" of DNA may denote methods such as that of Maxam and Gilbert (1977) (Proc. Natl. Acad. Sci. USA 74:560), in which DNA is randomly cleaved using individual base-specific reactions. "Enzymatic sequencing" of DNA may denote methods such as that of Sanger (Sanger, et al., (1977) Proc. Natl. Acad. Sci. USA 74:5463).

Conventional molecular biology, microbiology, and recombinant DNA techniques including sequencing techniques are well known among those skilled in the art. Such techniques are explained fully in the literature. See, e.g., Sambrook, Fritsch & Maniatis, Molecular Cloning: A Laboratory Manual, Second Edition (1989) Cold Spring Harbor Laboratory Press, Cold Spring Harbor, N.Y. (herein "Sambrook, et al., 1989"); DNA Cloning: A Practical Approach, Volumes I and II (D. N. Glover ed. 1985); Oligonucleotide Synthesis (M. J. Gait ed. 1984); Nucleic Acid Hybridization (B. D. Hames & S. J. Higgins eds. (1985)); Transcription And Translation (B. D. Hames & S. J. Higgins, eds. (1984)); Animal Cell Culture (R. I. Freshney, ed. (1986)); Immobilized Cells And Enzymes (IRL Press, (1986)); B. Perbal, A Practical Guide To Molecular Cloning (1984); F. M. Ausubel, et al. (eds.), Current Protocols in Molecular Biology, John Wiley & Sons, Inc. (1994

The Peptide Nucleic Acid (PNA) affinity assay is a derivative of traditional hybridization assays (Nielsen et al., Science 254:1497-1500 (1991); Egholm et al., J. Am. Chem. Soc. 114:1895-1897 (1992); James et al., Protein Science 3:1347-1350 (1994)). PNAs are structural DNA mimics that follow Watson-Crick base pairing rules, and are used in standard DNA hybridization assays. PNAs display greater specificity in hybridization assays because a PNA/DNA mismatch is more destabilizing than a DNA/DNA mismatch and complementary PNA/DNA strands form stronger bonds than complementary DNA/DNA strands.

DNA microarrays have been developed to detect genetic variations and polymorphisms (Taton et al., Science 289: 1757-60, 2000; Lockhart et al., Nature 405:827-836 (2000); Gerhold et al., Trends in Biochemical Sciences 24:168-73 (1999); Wallace, R. W., Molecular Medicine Today 3:384-89 (1997); Blanchard and Hood, Nature Biotechnology 149: 1649 (1996)). DNA microarrays are fabricated by high-speed robotics, on glass or nylon substrates, and contain DNA fragments with known identities ("the probe"). The microarrays are used for matching known and unknown DNA fragments ("the target") based on traditional base-pairing rules.

The Protein Truncation Test (PTT) is also commonly used to detect genetic polymorphisms (Roest et al., Human Molecular Genetics 2:1719-1721, (1993); Van Der Luit et al., Genomics 20:1-4 (1994); Hogervorst et al., Nature Genetics 10: 208-212 (1995)). Typically, in the PTT, the gene of interest is PCR amplified, subjected to in vitro transcription/translation, purified, and analyzed by polyacrylamide gel electrophoresis.

"Genetic testing" (also called genetic screening) as used herein refers to the testing of a biological sample from a subject to determine the subject's genotype; and may be utilized to determine if the subject's genotype comprises alleles that either cause, or increase susceptibility to, a particular phenotype (or that are in linkage disequilibrium with allele(s) causing or increasing susceptibility to that phenotype).

"Linkage disequilibrium" refers to the tendency of specific alleles at different genomic locations to occur together more frequently than would be expected by chance. Alleles at given loci are in complete equilibrium if the frequency of any particular set of alleles (or haplotype) is the product of their individual population frequencies A commonly used measure of linkage disequilibrium is r:

$$r = \frac{\hat{\Delta}_{AB}}{\sqrt{(\tilde{\pi}_A + \hat{D}_A)(\tilde{\pi}_B + \hat{D}_B)}}$$

where $$\tilde{\pi}_A = \tilde{p}_A(1-\tilde{p}_A), \tilde{\pi}_B = \tilde{p}_B(1-\tilde{p}_B), \hat{D}_A = \tilde{P}_{AA} - \tilde{p}_A^2, \hat{D}_B = \tilde{P}_{BB} - \tilde{p}_B^2$$

$$\hat{\Delta}_{AB} = \frac{1}{n}n_{AB} - 2\tilde{p}_A\tilde{p}_B$$

$nr^2$ has an approximate chi square distribution with 1 degree freedom for biallelic markers. Loci exhibiting an r such that $nr^2$ is greater than 3.84, corresponding to a significant chi-squared statistic at the 0.05 level, are considered to be in linkage disequilibrium (B S Weir 1996 Genetic Data Analysis II Sinauer Associates, Sunderland, Md.).

Alternatively, a normalized measure of linkage disequilibrium can be defined as:

$$D'_{AB} = \begin{cases} \frac{D_{AB}}{\min(p_Ap_B, p_ap_b)}, & D_{AB} < 0 \\ \frac{D_{AB}}{\min(p_Ap_b, p_ap_B)}, & D_{AB} > 0 \end{cases}$$

The value of the D' has a range of −1.0 to 1.0. When statistically significant absolute D' value for two markers is not less than 0.3 they are considered to be in linkage disequilibrium.

As used herein the phrase 'an HLA genotype' refers to a genotype that includes one of the HLA alleles for HLA-DQA1, HLA-DQB1 or HLA-DRB1, including HLA-DQA1*0201, HLA-DQB1*0202, and HLA-DRB1*0701.

As used herein the word "haplotype" refers to a set of closely linked HLA alleles present on one chromosome which tend to be inherited together. The DRB1*0701, DQB1*0202, DQA1*0201 combination of HLA genotypes is referred to as the DR7-DQ2 haplotype. An HLA genotype can be identified by detecting the presence of an HLA allele, or detecting a genetic marker known to be in linkage disequilibrium with an HLA allele. A genotype refers to variation at a defined position in a single gene, eg, 1,1 1,2 2,2. DQA1, DQB1 and DRB1 are distinct genes and proteins. Combinations of eg, DQA1*0201 and DQB1*0202 or DRB1*0701 would be a haplotype.

As used herein, determination of a multilocus' genotype (also known as a haplotype) refers to the detection within an individual of the alleles present at more than one locus. A subject may be genetically screened to determine the presence or absence of both an HLA allele (e.g., an HLA-DQA1*0201, HLA-DQB1*0202, or HLA-DRB1*0701 allele) and another allele, e.g, a different HLA allele or a non-HLA allele.

As used herein, the process of detecting an allele or polymorphism includes but is not limited to serologic and genetic methods. The allele or polymorphism detected may be functionally involved in affecting an individual's phenotype, or it may be an allele or polymorphism that is in linkage disequilibrium with a functional polymorphism/allele. Polymorphisms/alleles are evidenced in the genomic DNA of a subject, but may also be detectable from RNA, cDNA or protein sequences transcribed or translated from this region, as will be apparent to one skilled in the art.

Alleles, polymorphisms or genetic markers that are 'associated' with hepatotoxicity to a kinase inhibitor such as lapatinib, or a pharmaceutically acceptable salt or composition thereof, have been found to be over-represented in frequency in populations of treated subjects experiencing hepatotoxicity as compared to populations of treated subjects who do not experience hepatotoxicity, or as compared to the general population.

Accordingly, the present invention provides methods of treating a human for cancer comprising administering at least one dose of lapatinib, or a pharmaceutically acceptable salt or composition thereof, to the human, wherein said human does not have, or has been diagnosed as not having, one or more allelic polymorphisms selected from the group of: IILA-DQA1*0201, IILA-DQB1*0202, and IILA-DRB1*0701. In some instances, the human is free of at least two polymorphisms selected from the group of: HLA-DQA1*0201, HLA-DQB1*0202, and HLA-DRB1*0701. In some instances, the human is also free of a polymorphism selected from rs12153855 and rs17207923 that reside in the gene TNXB. In some instances, the human is also free from a polymorphism HLA-B*4403. In some instances, human is also free of the Gilbert's syndrome variant UGT1A1*28.

The present invention provides several methods treatment using the HLA marker(s). For instance, humans with certain HLA markers can be excluded from treatment with lapatinib. Patients can be tested and recorded for HLA allele status prior to the start of treatment. A patient can start treatment with lapatinib, if the patient subsequently experiences ALT elevation and/or hepatotoxicity, genetic information can be used to direct patient management. For example, but not restricted to, if a patient has ALT >3× and specified HLA allele is found, treatment may be discontinued. However, if ALT >3× and HLA genetic polymorphisms are absent treatment may continue. In some circumstances, a higher ALT thresholds (cg, >4×, >5×, or higher) may be used. The HLA alleles that are part of this invention are meant to be used to guide a clinician in providing treatment. Therefore, even a patient who is susceptible to hepatotoxicity in connection with lapatinib may start treatment with lapatinib with monitoring of liver signals. If liver signals increase, the patient's treatment dose of lapatinib may be lowered, terminated or suspended.

As used herein the word "treatment" includes administering a drug to a human subject for the amelioration, cure or prevention of disease, as well as providing such drug to a person administering the drug. The word "treatment" also includes assessing a human's hepatotoxicity or risk of experiencing hepatotoxicity, or HLA genotype or phenotype (e.g. a biomarker of the present invention), and administering a composition comprising a drug according to a method of the current invention, and further includes providing a service (e.g. central laboratory testing) to perform such assessing step(s), or providing a reagent (e.g. nucleotides, polypeptides, primers, probes, antibodies) or kit useful in performing such step(s) to a person performing such step(s). Thus, the word "treatment" further includes providing information useful for making a decision to administer a drug or for a manner of administering a drug, such as information about or from carrying out such assessing step(s), including, for example, information on lapatinib or a pharmaceutically acceptable salt or composition thereof, in accordance with the methods of the present invention. The word "treatment" still further includes administering lapatinib or a pharmaceutically acceptable salt or composition thereof in accordance with a method described on its label, or any amendment thereto.

In another embodiment of the present invention, lapatinib, or a pharmaceutically acceptable salt or composition thereof; is administered to said human as monotherapy. In another embodiment, lapatinib, or a pharmaceutically acceptable salt or composition thereof, is co-administered with at least one other anti-cancer agent. At least one other anti-cancer agent may be selected from, but not limited to, one or more of the group of: trastuzumab, capecitabine, paclitaxel, carboplatin, pazopanib and letrozole.

As used herein the term "co-administration" or "co-administering" and grammatical variation thereof mean either simultaneous administration or any manner of separate sequential administration of lapatinib, or a pharmaceutically acceptable salt or composition thereof, and a further active ingredient or ingredients including, but not limited to, chemotherapy and radiation treatment. The term further active ingredient or ingredients, as used herein, includes any compound or therapeutic agent known to or that demonstrates advantageous properties when administered to a patient in need of treatment. Furthermore, it does not matter if the compounds are administered in the same dosage form, e.g. one compound may be administered by injection and another compound may be administered orally. Co-administration of such compounds may be simultaneous or at about the same time (e.g., within the same hour) or it may be within several hours or days of one another. For example, a first compound may be administered once weekly while a second compound is co-administered daily. Additionally, the further active ingredient or ingredients may be administered for any condition, disease or disorder, including but not limited to, cancer and/or side effects of the treatment of cancer and/or manifestations of cancer.

As used herein "anti-cancer agent" includes, but is not limited to, any agent including but not limited to a chemotherapeutic agent, that has activity against a susceptible tumor. Examples of such agents can be found in Cancer Principles and Practice of Oncology by V. T. Devita and S. Hellman (editors), 6$^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Anti-cancer agents useful in the present invention include, but are not limited to, anti-microtubule agents such as diterpenoids and vinca alkaloids; platinum coordination complexes; alkylating agents such as nitrogen mustards, oxazaphosphorines, alkylsulfonates, nitrosoureas, and triazencs; antibiotic agents such as anthracyclins, actinomycins and bleomycins; topoisomerase II inhibitors such as epipodophyllotoxins; antimetabolites such as purine and pyrimidine analogues and anti-folate compounds; topoisomerase I inhibitors such as camptothecins; hormones and hormonal analogues; signal transduction pathway inhibitors; non-receptor tyrosine kinase angiogenesis inhibitors; immunotherapeutic agents; proapoptotic agents; and cell cycle signaling inhibitors. Also, as is understood in the art, commercially available, marketed drugs are described in their package insert along with methods of administering said drugs.

Anti-microtubule or anti-mitotic agents are phase specific agents active against the microtubules of tumor cells during M or the mitosis phase of the cell cycle. Examples of anti-microtubule agents include, but are not limited to, diterpenoids and vinca alkaloids. Diterpenoids, which are derived from natural sources, are phase specific anti-cancer agents that operate at the $G_2/M$ phases of the cell cycle. Examples of diterpenoids include, but are not limited to, paclitaxel and its analog docetaxel.

Paclitaxel, 5β,20-epoxy-1,2α,4,7β,10β,13α-hexa-hydroxytax-11-en-9-one 4,10-diacetate 2-benzoate 13-ester with (2R,3S)-N-benzoyl-3-phenylisoserine; is a natural diterpene product isolated from the Pacific yew tree *Taxus brevifolia* and is commercially available as an injectable solution TAXOL®. It is a member of the taxane family of terpenes. Docetaxel, (2R,3S)—N-carboxy-3-phenylisoserine,N-tert-butyl ester, 13-ester with 5β-20-epoxy-1,2α,4,7β,10β,13α-hexahydroxytax-11-en-9-one 4-acetate 2-benzoate, trihydrate, is commercially available as an injectable solution as TAXOTERE®.

Vinca alkaloids are phase specific anti-neoplastic agents derived from the periwinkle plant. Examples of vinca alkaloids include, but are not limited to, vinblastine, vincristine, and vinorelbine. Vinblastine, vincaleukoblastine sulfate, is commercially available as VELBAN® as an injectable solution. Vincristine, vincaleukoblastine, 22-oxo-, sulfate, is commercially available as ONCOVIN® as an injectable solution. Vinorelbine, 3',4'-didehydro-4'-deoxy-C'-norvincaleukoblastine [R-(R*,R*)-2,3-dihydroxybutanedioate (1:2)(salt)], commercially available as an injectable solution of vinorelbine tartrate (NAVELBINE®), is a semisynthetic vinca alkaloid.

Platinum coordination complexes are non-phase specific anti-cancer agents, which are interactive with DNA. Examples of platinum coordination complexes include, but are not limited to, cisplatin and carboplatin. Cisplatin, cis-diaminedichloroplatinum, is commercially available as PLATINOL® as an injectable solution. Carboplatin, platinum, diammine[1,1-cyclobutane-dicarboxylate(2-)-O,O], is commercially available as PARAPLATIN® as an injectable solution.

Alkylating agents are non-phase anti-cancer specific agents and strong electrophiles. Typically, alkylating agents form covalent linkages, by alkylation, to DNA through nucleophilic moieties of the DNA molecule such as phosphate, amino, sulfhydryl, hydroxyl, carboxyl, and imidazole groups. Such alkylation disrupts nucleic acid function leading to cell death. Examples of alkylating agents include, but are not limited to, nitrogen mustards such as cyclophosphamide, melphalan, and chlorambucil; alkyl sulfonates such as busulfan; nitrosoureas such as carmustine; and triazenes such as dacarbazine.

Cyclophosphamide, 2-[bis(2-chloroethyl)amino]tetrahydro-2H-1,3,2-oxazaphosphorine 2-oxide monohydrate, is commercially available as an injectable solution or tablets as CYTOXAN®. Melphalan, 4-[bis(2-chloroethyl)amino]-L-phenylalanine, is commercially available as an injectable solution or tablets as ALKERAN®. Chlorambucil, 4-[bis(2-chloroethyl)amino]benzenebutanoic acid, is commercially available as LEUKERAN® tablets. Busulfan. 1,4-butanediol dimethanesulfonate, is commercially available as MYLERAN® TABLETS. Carmustine, 1,3-[bis(2-chloroethyl)-1-nitrosourea, is commercially available as single vials of lyophilized material as BiCNU®. Dacarbazine, 5-(3,3-dimethyl-1-triazeno)-imidazole-4-carboxamide, is commercially available as single vials of material as DTIC-Dome®.

Antibiotic anti-cancer agents are non-phase specific agents, which bind or intercalate with DNA. Examples of antibiotic anti-cancer agents include, but are not limited to, actinomycins such as dactinomycin, anthrocyclins such as daunorubicin and doxorubicin; and bleomycins. Dactinomycin, also known as Actinomycin D, is commercially available in injectable form as COSMEGEN®. Daunorubicin, (8S-cis-)-8-acetyl-10-[(3-amino-2,3,6-trideoxy-α-L-lyxohexopyranosyl)oxy]-7,8,9,10-tetrahydro-6,8,11-trihydroxy-1-methoxy-5,12 naphthacenedione hydrochloride, is commercially available as a liposomal injectable form as DAUNOXOME® or as an injectable as CERUBIDINE®. Doxorubicin, (8S,10S)-10-[(3-amino-2,3,6-trideoxy-α-L-lyxo-hexopyranosyl)oxy]-8-glycoloyl, 7,8,9,10-tetrahydro-6,8,11-trihydroxy-1-methoxy-5,12 naphthacenedione hydrochloride, is commercially available as an injectable form as RUBEX® or ADRIAMYCIN RDF®. Bleomycin, a mixture of cytotoxic glycopeptide antibiotics isolated from a strain of *Streptomyces verticillus*, is commercially available as BLENOXANE®.

Topoisomerase II inhibitors include, but are not limited to, epipodophyllotoxins. Examples of epipodophyllotoxins include, but are not limited to, etoposide and teniposide. Etoposide, 4'-demethyl-epipodophyllotoxin 9[4,6-0-(R)-ethylidene-β-D-glucopyranoside], is commercially available as an injectable solution or capsules as VEPESID® and is commonly known as VP-16. Teniposide, 4'-demethyl-epipodophyllotoxin 9[4,6-0-(R)-thenylidene-β-D-glucopyranoside], is commercially available as an injectable solution as VUMON® and is commonly known as VM-26.

Antimetabolite neoplastic agents are phase specific anti-cancer agents that act at S phase (DNA synthesis) of the cell cycle by inhibiting DNA synthesis or by inhibiting purine or pyrimidine base synthesis and thereby limiting DNA synthesis. Consequently, S phase does not proceed and cell death follows. Examples of antimetabolite anti-neoplastic agents include, but are not limited to, fluorouracil, methotrexate, cytarabine, mecaptopurine, thioguanine, and gemeitabine. 5-fluorouracil, 5-fluoro-2,4-(1H,3H) pyrimidinedione, is commercially available as fluorouracil. Cytarabine, 4-amino-1-β-D-arabinofuranosyl-2(1H)-pyrimidinone, is commercially available as CYTOSAR-U® and is commonly known as Ara-C. Mercaptopurine, 1,7-dihydro-6H-purine-6-thione monohydrate, is commercially available as PURINETHOL®. Thioguanine, 2-amino-1,7-dihydro-6H-purine-6-thione, is commercially available as TABLOID®. Other purine analogs include pentostatin, erythrohydroxynonyladenine, fludarabine phosphate, and eladribine. Gemcitabine, 2'-deoxy-2',2'-difluorocytidine monohydrochloride (β-isomer), is commercially available as GEMZAR®. Methotrexate, N-[4[[(2,4-diamino-6-pteridinyl)methyl]methylamino]benzoyl]-glutamic acid, is commercially available as methotrexate sodium.

Capecitabine, pentyl[1-(3,4-dihydroxy-5-methyl-tetrahydrofuran-2-yl)-5-fluoro-2-oxo-1H-pyrimidin-4-yl]aminomethanoate, is an orally-administered chemotherapeutic agent used in the treatment of metastatic breast and colorectal cancers and is available as XELODA®. Capecitabine is a prodrug, that is enzymatically converted to 5-fluorouracil in the tumor, where it inhibits DNA synthesis and slows growth of tumor tissue.

Camptothecins, including, camptothecin and camptothecin derivatives are available or under development as Topoisomerase I inhibitors. Irinotecan HCl, (4S)-4,11-diethyl-4-hydroxy-9[(4-piperidinopiperidino)carbonyloxy]-1H-pyrano[3',4',6,7]indolizino[1,2-b]quinoline-3,14(4H,12H)-dione hydrochloride, is commercially available as the injectable solution CAMPTOSAR®. Topotecan HCl, (S)-10-[(dimethylamino)methyl]-4-ethyl-4.9-dihydroxy-1H-pyrano[3',4',6,7]indolizino[1,2-b]quinoline-3,14-(4H,12H)-dione monohydrochloride, is commercially available as the injectable solution HYCAMTIN®.

Other anti-cancer agents include signal transduction pathway inhibitors which are those inhibitors, which block or inhibit a chemical process which evokes an intracellular change. As used herein this change is cell proliferation or differentiation. Signal transduction inhibitors include inhibitors of receptor tyrosine kinases, non-receptor tyrosine kinases, SH2/SH3 domain blockers, serine/threonine kinases, phosphotidylinositol-3 kinases, myo-inositol signaling, and Ras oncogenes. Several protein tyrosine kinases catalyse the phosphorylation of specific tyrosyl residues in various proteins involved in the regulation of cell growth. Such protein tyrosine kinases can be broadly classified as receptor or non-receptor kinases.

Receptor tyrosine kinases are transmembrane proteins having an extracellular ligand binding domain, a transmembrane domain, and a tyrosine kinase domain. Receptor tyrosine kinases are involved in the regulation of cell growth and are generally termed growth factor receptors. Inappropriate or uncontrolled activation of many of these kinases, i.e. aberrant kinase growth factor receptor activity, for example by over-expression or mutation, has been shown to result in uncontrolled cell growth. Accordingly, the aberrant activity of such kinases has been linked to malignant tissue growth. Consequently, inhibitors of such kinases could provide cancer treatment methods. Growth factor receptors include, for example, epidermal growth factor receptor (EGFr), platelet derived growth factor receptor (PDGFr), erbB2, erbB4, vascular endothelial growth factor receptor (VEGFr), tyrosine kinase with immunoglobulin-like and epidermal growth factor homology domains (TIE-2), insulin growth factor-I (IGFI) receptor, macrophage colony stimulating factor (cfms), BTK, ckit, cmet, fibroblast growth factor (FGF) receptors, Trk receptors (TrkA, TrkB, and TrkC), ephrin (eph) receptors, and the RET protooncogene. Several inhibitors of growth receptors are under development and include ligand antagonists, antibodies, tyrosine kinase inhibitors and anti-sense oligonucleotides. Growth factor receptors and agents that inhibit growth factor receptor function are described, for instance, in Kath, John C., Exp. Opin. Ther. Patents (2000) 10(6):803-818; Shawver et al DDT Vol 2, No. 2 Feb. 1997; and Lofts, F. J. et al, "Growth factor receptors as targets", New Molecular Targets for Cancer Chemotherapy, ed. Workman, Paul and Kerr, David, CRC press 1994, London.

Tyrosine kinases, which are not growth factor receptor kinases are termed non-receptor tyrosine kinases. Non-receptor tyrosine kinases for use in the present invention, which are targets or potential targets of anti-cancer drugs, include cSrc, Lck, Fyn, Yes, Jak, cAbl, FAK (Focal adhesion kinase), Brutons tyrosine kinase, and Bcr-Abl. Such non-receptor kinases and agents which inhibit non-receptor tyrosine kinase function are described in Sinh, S. and Corey, S. J., (1999) Journal of Hematotherapy and Stem Cell Research 8 (5): 465-80; and Bolen, J. B., Brugge, J. S., (1997) Annual review of Immunology. 15: 371-404.

SH2/SH3 domain blockers are agents that disrupt SH2 or SH3 domain binding in a variety of enzymes or adaptor proteins including, PI3-K p85 subunit. Src family kinases, adaptor molecules (She, Crk, Nck, Grb2) and Ras-GAP. SH2/SH3 domains as targets for anti-cancer drugs are discussed in Smithgall, T. E. (1995), Journal of Pharmacological and Toxicological Methods. 34(3) 125-32.

Inhibitors of Serine/Threonine Kinases including MAP kinase cascade blockers which include blockers of Raf kinases (rafk), Mitogen or Extracellular Regulated Kinase (MEKs), and Extracellular Regulated Kinases (ERKs); and Protein kinase C family member blockers including blockers of PKCs (alpha, beta, gamma, epsilon, mu, lambda, iota, zeta). IkB kinase family (IKKa, IKKb), PKB family kinases, akt kinase family members, and TGF beta receptor kinases. Such Serine/Threonine kinases and inhibitors thereof are described in Yamamoto, T., Taya, S., Kaibuchi, K., (1999), Journal of Biochemistry. 126 (5) 799-803; Brodt, P, Samani, A., and Navab, R. (2000), Biochemical Pharmacology, 60. 1101-1107; Massague, J., Weis-Garcia, F. (1996) Cancer Surveys. 27:41-64; Philip, P. A., and Harris, A. L. (1995), Cancer Treatment and Research. 78: 3-27, Lackey, K. et al Bioorganic and Medicinal Chemistry Letters, (10), 2000, 223-226; U.S. Pat. No. 6,268,391; and Martinez-Iacaci, L., et al, Int. J. Cancer (2000), 88(1), 44-52.

Commercially available protein kinase inhibitors include, but are not limited to, bevacizumab, cetuximab, imatinib, trastuzumab, gefitinib, ranibizumab, pegaptanib, sorafenib, dasatinib, sunitinib, erlotinib, nilotinib, lapatinib, pazoponib, and panitumumab. Bevacizumab, is a humanized monoclonal antibody that recognizes and blocks vascular endothelial growth factor A (VEGF-A) and is available as AVASTIN®. Cetuximab is a mouse/human chimeric antibody that recognizes epidermal growth factor receptor (EGF) and is available as ERBITUX®. Imatinib, 4-[(4-methylpiperazin-1-yl)methyl]-N-[4-methyl-3-[(4-pyridin-3-ylpyrimidin-2-yl)amino]phenyl]benzamide, is available as GLEEVEC® or GLIVEC®. Trastuzumab, is a humanized mouse monoclonal antibody that interferes with the HER2/neu receptor also known as Erb2 and is commercially available as HERCEPTIN®. Gefitinib, N-(3-chloro-4-fluoro-phenyl)-7-methoxy-6-(3-morpholin-4-ylpropoxy) quinazolin-4-amine, is an EGFR inhibitor available as IRESSA. Ranibizumab is a monoclonal antibody fragment (Fab) derived from the same parent murine antibody as bevacizumab (AVASTIN®) and is available as LUCENTIS®. Sorafenib, 4-[4[[4-chloro-3-(trifluoromethyl)phenyl] carbamoylamino]phenoxy]-N-methyl-pyridine-2-carboxamide, is a marketed as NEXAVAR®. Dasatinib, N-(2-chloro-6-methylphenyl)-2-[[6-[4-(2-hydroxyethyl)-1-piperazinyl]-2-methyl-4-pyrimidinyl]amino]-5-thiazole carboxamide monohydrate, is available as SPRYCEL®. Erlotinib, N-(3-ethynylphenyl)-6,7-bis(2-methoxyethoxy) quinazolin-4-amine, is available as TARCEVA®. Nilotinib, 4-methyl-N-[3-(4-methyl-1H-imidazol-1-yl)-5-(trifluoromethyl)phenyl]-3-[(4-pyridin-3-ylpyrimidin-2-yl)amino]benzamide, is a BCR-ABL inhibitor and is available as TASIGNA®. Pazopanib, 5-[[4-[(2,3-Dimethyl-2H-indazol-6-yl)methylamino]-2-pyrimidinyl]amino]-2-methylbenzolsulfonamide, is a VEGFR inhibitor which is commercially available as VOTRIENT®. Panitumumab is a fully human monoclonal antibody specific to the epidermal growth factor receptor (also known as EGF receptor, EGFR, ErbB-1 and HER1 in humans) and is marketed as VECTIBIX®.

Hormones and hormonal analogues are useful compounds for treating cancers in which there is a relationship between the hormone(s) and growth and/or lack of growth of the cancer. Examples of hormones and hormonal analogues useful in cancer treatment include, but are not limited to, adrenocorticosteroids such as prednisone and prednisolone which are useful in the treatment of malignant lymphoma and acute leukemia in children; aminoglutethimide and other aromatase inhibitors such as anastrozole, letrazole, vorazole, and exemestane useful in the treatment of adrenocortical carcinoma and hormone dependent breast carcinoma containing estrogen receptors; progestrins such as megestrol acetate useful in the treatment of hormone dependent breast cancer and endometrial carcinoma; estrogens, androgens, and anti-androgens such as flutamide, nilutamide, bicalutamide, cyproterone acetate and 5α-reductases such as finasteride and dutasteride, useful in the treatment of prostatic carcinoma and benign prostatic hypertrophy; anti-estrogens such as tamoxifen, toremifene, raloxifene, droloxifene, iodoxyfene, as well as selective estrogen receptor modulators (SERMS) such those described in U.S. Pat. Nos. 5,681, 835, 5,877,219, and 6,207,716, useful in the treatment of hormone dependent breast carcinoma and other susceptible cancers; and gonadotropin-releasing hormone (GnRH) and analogues thereof which stimulate the release of leutinizing hormone (LH) and/or follicle stimulating hormone (FSH) for the treatment prostatic carcinoma, for instance, LHRH agonists and antagagonists such as goserelin acetate and luprolide. Letrozole, 4-[(4-cyanophenyl)-(1,2,4-triazol-1-yl) methyl]benzonitrile, is an oral non-steroidal aromatase inhibitor for the treatment of hormonally-responsive breast cancer after surgery and is available as FEMARA®.

In yet another embodiment, the human shows a statistically significantly less hepatotoxicity when administered lapatinib, or a pharmaceutically acceptable salt or composition thereof, compared with a human having at least one polymorphism selected from the group of: HLA-DQA1*0201, HLA-DQB1*0202, and HLA-DRB1*0701. In another aspect, the human does not show significant elevation in ALT and/or TBL after the administration of at least one dose of lapatinib, or a pharmaceutically acceptable salt or composition thereof. In some instances, a human subject may be seropositive for DQ2.2 which may serve as an indication of HLA-DQA1*0201, HLA-DQB1*0202 polymorphism.

In yet another embodiment of the present invention, methods are provided for screening a human subject as an aid in predicting hepatotoxicity to lapatinib administration, or administration a pharmaceutically acceptable salt or composition thereof, comprising determining whether the subject has a HLA genotype associated with an increased risk of hepatotoxicity to lapatinib, or a pharmaceutically acceptable salt or composition thereof, compared to the risk expected in the general population, wherein the presence of such a HLA genotype indicates the subject is at increased risk for a hepatotoxicity to lapatinib, or a pharmaceutically acceptable salt or composition thereof. In some instances the methods comprise treating said subject with a therapeutic regime of lapatinib when the subject is not at increased risk of a hepatotoxicity to lapatinib, or a pharmaceutically acceptable salt or composition thereof. In some instances, the HLA genotype is selected from the group of: HLA-DQA1*0201, HLA-DQB1*0202, and HLA-DRB1*0701. Some methods further comprise correlating the detection of an HLA-DQA1*0201, HLA-DQB1*0202, HLA-DRB1*0701, and/ or HLA-B*4403 allele with an increased risk of experiencing hepatotoxicity to lapatinib, or a pharmaceutically acceptable salt or composition thereof. Some methods further comprise determining if a human subject has a genotype in TNXB rs12153855 and/or rs17207923 and correlating that genotype with an increased risk of of experiencing hepatotoxicity to lapatinib. In some instances, the human subject may have both HLA-DQA1*0201 and HLA-DQB1*0202 polymorphisms and/or may be DQ2.2 seropositive. HLA Class II peptides form heterodimer proteins where DQA1/DQB1 and DRA/DRB1 combinations create discrete antigen binding sites (Jones E Y, et al. Nature Reviews: Immunology 2006; 6; 271-282). HLA-DRA is functionally monomorphic and no further marker discrimination can be gained by evaluating specific allelic combinations. In contrast, both DQA1*0201 and DQB1*0202 are polymorphic. DQA1*0201 typically forms cis-haplotype isoforms with DQB1*0202 (DQ2.2) or DQB1*0303 (DQ9.2), while a DQ2.2 trans isoform can be created by an individual carrying DQ9.2 and DQ2.5 (DQB1*0201/DQA1*0501) (Fallang, et al, Nature Immunology 2009; 10; 1096-1102). Therefore we investigated alleles that contribute to the DQ2.2 serotype, comprising DQA1*0201 as α peptide, with DQB1*0201, *0202 and *0204 (designated as DQB1*0201g) as cis or trans β peptides (Jones E Y, et al. Nature Reviews: Immunology 2006; 6; 271-282) on ALT elevation in the confirmatory study.

In another embodiment methods are provided of treating a human subject in need of treatment with lapatinib, or a pharmaceutically acceptable salt or composition thereof, the method comprising:
   determining the genotype of the human at HLA-DQA1, HLA-DQB1, HLA-DRB1, and/or HLA-B regions of chromosome 6; and
   administering lapatinib, or a pharmaceutically acceptable salt or composition thereof, to said human if polymorphic allele in an HLA gene is not detected.

In some instances the HLA gene is a Class II HLA gene. The polymorphic allele is selected from the group of: HLA-DQA1*0201. HLA-DQB1*0202, and HLA-DRB1*0701 and optionally the human has at least one additional polymorphic allele. In some instances, the human also has at least one polymorphic genotype in TNXB selected from: rs12153855 and rs17207923.

Methods are also provided for prescribing lapatinib, or a pharmaceutically acceptable salt or composition thereof, to a human subject diagnosed with a medical condition suitable for treatment with lapatinib, or a pharmaceutically acceptable salt or composition thereof, comprising:
   determining whether the human subject has an HLA genotype that has been
   associated with increased risk of hepatotoxicity, compared to the risk in the general population, and
   where said human subject is not determined to have a genotype that has been associated with increased risk hepatotoxicity, prescribing treatment with lapatinib, or a pharmaceutically acceptable salt or composition thereof, to said subject.

HLA genotype that has been associated with an increased risk of hepatotoxicity is selected from the group of: HLA-DQA1*0201, HLA-DQB1*0202, and HLA-DRB1*0701. Additionally, the human may have the genotype HLA-B*4403.

Methods for genotyping or determining HLA genotype include, but are not limited to, methods that detect the presence of the allelic DNA sequence.

Also provided are methods of administering lapatinib, or a pharmaceutically acceptable salt or composition thereof, to reduce the incidence of hepatotoxicity, comprising:

from a starting population of human subjects having a condition suitable for treatment with lapatinib, or a pharmaceutically acceptable salt or composition thereof, selecting a treatment population having a decreased percentage of human subjects with an polymorphic allele in HLA compared to the starting population; and administering lapatinib, or a pharmaceutically acceptable salt or composition thereof, to said treatment population;

whereby the incidence of hepatotoxicity is reduced in the treatment population compared to the incidence of hepatotoxicity that would be expected to occur in the starting population.

Also provided are methods of identifying a human subject at increased risk of experiencing a hypersensitivity reaction to a therapeutic regime of lapatinib, or a pharmaceutically acceptable salt or composition thereof, comprising:

performing a genotyping technique on a biological sample from said human subject to determine whether the subject's HLA genotype includes an allele selected from HLA-DQA1*0201 HLA-DQB1*0202, or HLA-DRB1*0701;

detecting an HLA-DQA1*0201, HLA-DQB1*0202, and/or HLA-DRB1*0701 allele; and correlating the detection of an HLA-DQA1*0201, HLA-DQB1*0202, and/or HLA-DRB1*0701 allele with an increased risk of experiencing a hepatotoxicity to a therapeutic regime of lapatinib, or a pharmaceutically acceptable salt or composition thereof, compared to the risk if no HLA-DQA1*0201, HLA-DQB1*0202, and/or HLA-DRB1*0701 allele were detected.

A subject may also be further identified for increased risk of hepatotoxicity to lapatinib by genotyping said subject for HLA-B*4403 and/or a polymorphism in TXNB and correlating that genotype with an increased risk of hepatotoxicity.

Biological samples for testing of one or more polymorphisms may be selected from the group of proteins, nucleotides, cellular blebs or components, serum, cells, blood, blood components, urine and saliva. Testing for polymorphisms may be conducted by several techniques known in the art and/or described herein.

Another embodiment provides methods for treatment of a human subject with lapatinib, or a pharmaceutically acceptable salt or composition thereof, who have, or who have been diagnosed as having, Her2 overexpressing breast cancer and/or HER2 amplification and have received prior therapy including one or more of an anthracycline, a taxane, and trastuzumab, and who do not have, or have been diagnosed as not having, one or more allelic polymorphisms selected from the group of: HLA-DQA1*0201, HLA-DQB1*0202 and HLA-DRB1*0701.

Still another embodiment provides methods comprising a step of HLA genotyping of a human subject being treated with lapatinib, or a pharmaceutically acceptable salt or composition thereof, who has a liver safety signal, and optionally providing a step of continuing treatment with lapatinib, or a pharmaceutically acceptable salt or composition thereof, with safety monitoring of such subject, which subject does not have, or has been diagnosed to not have, one or more allelic polymorphisms selected from the group of: HLA-DQA1*0201, HLA-DQB1*0202, and HLA-DRB1*0701. In yet another embodiment of the invention "polymorphic allele" includes one or more alleles within a gene, a surrogate allele or marker for an allele within such gene, an allele or marker on human chromosome 6 that is within about 6 megabase pairs from such gene or in the MHC region, and an allele or marker that is in linkage disequilibrium with an allele or marker in such gene, wherein such gene may be one or more of HLA-DQA1, HLA-DQB1, HLA-DRB1, HLA-B and UGT1A1.

Methods of the invention may be used with human subjects diagnosed with or suffering from any cancer, including but not limited to cancer that is susceptible to inhibition of EGFR, erbB-2, or Akt, as well as both primary and metastatic forms of head and neck, breast, lung, colon, ovary, and prostate cancers. The methods may also be used for any human subject being treated with lapatinib.

The invention also provides methods of treating a human for cancer comprising administering at least one dose lapatinib, or a pharmaceutically acceptable salt or composition thereof, to said human, monitoring the level of ALT and/or total bilirubin (TBL) in from said human, genotyping said human for one or more allelic polymorphisms selected from the group of: HLA-DQA1*0201, HLA-DQB1*0202, and HLA-DRB1*0701 if said human demonstrates an elevation in said ALT above 3.0×ULN and/or said total bilirubin is above 1.5×ULN to about or above 2×ULN. This method further comprises administering at least a second dose of lapatinib to said human if said human does not have one or more allelic polymorphisms selected from the group of: HLA-DQA1*0201, HLA-DQB1*0202, and HLA-DRB1*0701 Liver signal such as ALT and/or TBL can be measured using techniques well known in the art from samples including blood, serum and plasma samples. In some instances the human is suffering from breast cancer. In humans who do not have at least one of the following polymorphisms: HLA-DQA1*0201, HLA-DQB1*0202, and HLA-DRB1*0701, but who demonstrate elevated liver signals, liver signals such as ALT and TBL can continue to be monitored while the human subject remains on drug. If these or other liver signals remain elevated above 3.0×ULN, then lapatinib treatment can be discontinued or suspended until liver signals return to normal range. Lapatinib treatment may be restarted.

The invention also provides of administering lapatinib, or a pharmaceutically acceptable salt or composition thereof, to a human comprising:

(a) administering at least a first dose of lapatinib, (b) monitoring at least one liver signal in said human, (c) genotyping said human for one or more allelic polymorphisms selected from the group of: HLA-DQA1*0201, HLA-DQB1*0202, and HLA-DRB1*0701 if said liver signal becomes elevated after receiving at least one dose of lapatinib; and (d) administering at least a second dose of lapatinib to said human if the human does not have any of the polymorphisms of step (c). In certain aspects the liver signal are selected from ALT and TBL. In other aspects, the human is suffering from breast cancer. ALT maybe elevated to above 3.0×ULN and/or TBL may be elevated in said human to above 1.5×ULN or above 2.0 ULN after at least one dose of lapatinib. These liver signals may not become elevated until more than one dose of lapatinib has been administered to said human. Periodic monitoring of liver signals can be performed and genotyping may occur after the liver signal is elevated to above the normal range for that liver signal. Liver signals such as ALT may not be elevated to 3.0×ULN after only one dose of lapatinib, or a pharmaceutically acceptable salt or compositor thereof, but may increase after two or more doses of lapatinib. As is understood in the art, liver signals may not start to elevate in a human receiving therapy regardless of HLA polymorphisms after only one dose of therapy. In some instances, liver signal elevation may be gradual and may not occur for one week, one month or up to or over 100 days after the start of therapy. Thus, liver signals such as ALT can be monitored at intervals and genotyping may occur only after a particular liver signal level is reached.

Lapatinib may increase serum total bilirubin (TBL) levels. A post-hoc pharmacogenetic investigation of lapatinib induced TBL elevations has been conducted in patients who participated in AMBC clinical trials and received lapatinib as monotherapy or in combination with various chemotherapies (see above). Studies have shown that the (TA)7/(TA)7 genotype of UGT1A1 (UGT1A1*28/*28, which confers an underlying genetic susceptibility to Gilbert's Syndrome) can increase serum total bilirubin (TBL) levels during drug treatment. In this analysis, the (TA)7/(TA)7 genotype was associated with a statistically significant increase in the risk of lapatinib induced hyperbilirubinemia, relative to the (TA)6/(TA)6 and (TA)6/(TA)7 genotypes. Additionally, the prevalence of UGT1A1 (TA)7/(TA)7 genotype that results in hyperbilirubinemia differs according to race/ethnicity. Thus, in one aspect of the present invention, methods are provide for administering lapatinib to a human wherein said human is free of a (TA)7/(TA)7 genotype of UGT1A1. Additionally, a human demonstrating an increase in total bilirubin levels after the administration of at least one dose of lapatinib can be tested for fractionationated bilirubin by blood test. Means of testing for fractionated bilirubin are well known in the art. In a subject having an increase of ALT above 3×ULN and having at least one genotype selected from HLA-DQA1*0201, HLA-DQB1*0202, and/or HLA-DRB1*0701 the subject can be further tested for fractionated bilirubin.

The inventors established that a correlation exists between an individual's HLA genotype (particularly class II), and the risk of experiencing a hepatotoxicity after lapatinib administration, or administration of a pharmaceutically acceptable salt or composition thereof. Accordingly, the invention provides a method of assessing an individual's relative risk of hepatotoxicity involves genotyping that individual at the HLA genes to determine whether the individual's genotype places them at increased risk of hepatotoxicity. Individuals possessing an IILA genotype that has been previously associated with an increased incidence of hepatotoxicity (compared to the incidence of hepatotoxicity in subjects with alternate genotypes) are at increased risk of hepatotoxicity.

The present screening methods comprise genotyping a subject at HLA genes, particularly the HLA class II genes, including to detect the presence or absence of IILA-DQA1*0201, IILA-DQB1*0202, IILA-DRB1*0701, and/or IILA-B*4403.

In view of the present disclosure, it will be apparent to one skilled in the art how to determine additional genotypes that are associated with an increased risk of hepatotoxicity. Various allelic forms of HLA genes are known, and methods of typing HLA genes are known in the art. As additional polymorphisms are detected in human HLA genes, typing for such polymorphisms may be based on known methods. Accordingly, one may type a population of subjects who have received lapatinib, or a pharmaceutically acceptable salt or composition thereof, and correlate HLA genotype with the occurrence of hepatotoxicity. In an alternate method, one may genotype only those subjects who have experienced hepatotoxicity and, where the prevalence of an HLA allele is known in a matched control (non-hepatotoxic) population, determine whether the allele is over-represented in the hepatotoxic population, indicating that it is associated with hepatotoxicity. As will be apparent to one skilled in the art, the detection of an HLA allele may be accomplished by typing for genetic markers that are known to be in linkage disequilibrium with the target HLA allele/polymorphism. Preferably such markers are in substantial linkage disequilibrium, more preferably the markers are in complete linkage disequilibrium.

It will be apparent to those skilled in the art that, as multiple HLA genotypes exist, the relative risk of hepatotoxicity may vary among the multiple genotypes. For example, in a multilocus screening method where more than two genotypes are found, relative risk may be determined to be highest for one genotype, lowest for another, and intermediate in others. 'Increased risk' may be as compared to the risk in a population that has not been stratified by genotype (a general population), or, when further identified, "increased risk" is as compared to the risk expected in another defined genotype.

The presence of a particular predetermined genotype that is associated with an increased risk of hepatotoxicity therefore indicates an increased likelihood that the individual will exhibit the associated phenotype (hepatotoxicity) relative to subjects with one or more alternate genotypes. The genotype will rarely be absolutely predictive, i.e., where a population with a certain genotype displays a high incidence of an associated phenotype, not every individual with that genotype will display the phenotype. Likewise, some individuals with a different genotype may display the same phenotype. However, it will be apparent to those skilled in the art that genotyping a subject as described herein will be an aid in predicting a subject's risk of hepatotoxicity to treatment with lapatinib, or a pharmaceutically acceptable salt or composition thereof, and thus assist in treatment decisions. The present methods may further comprise administering lapatinib, or a pharmaceutically acceptable salt or composition thereof, to subjects after screening in subjects where the risk of hepatotoxicity is deemed acceptable; the final treatment decision will be based on factors in addition to genetic testing (as will be readily apparent to one skilled in the art), including the subject's overall health status and expected treatment outcome.

Polymorphic alleles may be detected by determining the DNA polynucleotide sequence, or by detecting the corresponding sequence in RNA transcripts from the polymorphic gene, or where the nucleic acid polymorphism results in a change in an encoded protein by detecting such amino acid sequence changes in encoded proteins; using any suitable technique as is known in the art. Polynucleotides utilized for typing are typically genomic DNA, or a polynucleotide fragment derived from a genomic polynucleotide sequence, such as in a library made using genomic material from the individual (e.g., a cDNA library). The polymorphism may be detected in a method that comprises contacting a polynucleotide or protein sample from an individual with a specific binding agent for the polymorphism and determining whether the agent binds to the polynucleotide or protein, where the binding indicates that the polymorphism is present. The binding agent may also bind to flanking nucleotides and amino acids on one or both sides of the polymorphism, for example at least 2, 5, 10, 15 or more flanking nucleotide or amino acids in total or on each side. In the case where the presence of the polymorphism is being determined in a polynucleotide it may be detected in the double stranded form, but is typically detected in the single stranded form.

The binding agent may be a polynucleotide (single or double stranded) typically with a length of at least 10 nucleotides, for example at least 15, 20, 30, or more nucleotides. A polynucleotide agent which is used in the method will generally bind to the polymorphism of interest, and the flanking sequence, in a sequence specific manner (e.g. hybridize in accordance with Watson-Crick base pairing) and thus typically has a sequence which is fully or partially complementary to the sequence of the polymorphism and flanking region. The binding agent may be a molecule that is structurally similar to polynucleotides that comprises units (such as purine or pyrimidine analogs, peptide nucleic acids, or RNA derivatives such as locked nucleic acids (LNA)) able to participate in Watson-Crick base pairing. The agent may be a protein, typically with a length of at least 10 amino acids, such as at least 20, 30, 50, or 100 or more amino acids. The agent may be an antibody (including a fragment of such an antibody that is capable of binding the polymorphism).

In one embodiment of the present methods a binding agent is used as a probe. The probe may be labelled or may be capable of being labelled indirectly. The detection of the label may be used to detect the presence of the probe on (bound to) the polynucleotide or protein of the individual. The binding of the probe to the polynucleotide or protein may be used to immobilize either the probe or the polynucleotide or protein (and, thus, to separate it from one composition or solution).

In another embodiment of the invention the polynucleotide or protein of the individual is immobilized on a solid support and then contacted with the probe. The presence of the probe immobilized to the solid support (via its binding to the polymorphism) is then detected, either directly by detecting a label on the probe or indirectly by contacting the probe with a moiety that binds the probe. In the case of detecting a polynucleotide polymorphism the solid support is generally made of nitrocellulose or nylon. In the case of a protein polymorphism the method may be based on an ELISA system.

The present methods may be based on an oligonucleotide ligation assay in which two oligonucleotide probes are used. These probes bind to adjacent areas on the polynucleotide which contains the polymorphism, allowing (after binding) the two probes to be ligated together by an appropriate ligase enzyme. However the two probes will only bind (in a manner which allows ligation) to a polynucleotide that contains the polymorphism, and therefore the detection of the ligated product may be used to determine the presence of the polymorphism.

In one embodiment the probe is used in a heteroduplex analysis based system to detect polymorphisms. In such a system when the probe is bound to a polynucleotide sequence containing the polymorphism, it forms a heteroduplex at the site where the polymorphism occurs (i.e. it does not form a double strand structure). Such a heteroduplex structure can be detected by the use of an enzyme that is single or double strand specific. Typically the probe is an RNA probe and the enzyme used is RNAse H that cleaves the heteroduplex region, thus, allowing the polymorphism to be detected by means of the detection of the cleavage products.

The method may be based on fluorescent chemical cleavage mismatch analysis which is described for example in *PCR Methods and Applications* 3:268-71 (1994) and *Proc. Natl. Acad. Sci.* 85:4397-4401 (1998).

In one embodiment the polynucleotide agent is able to act as a primer for a PCR reaction only if it binds a polynucleotide containing the polymorphism (i.e. a sequence- or allele-specific PCR system). Thus, a PCR product will only be produced if the polymorphism is present in the polynucleotide of the individual, and the presence of the polymorphism is determined by the detection of the PCR product. The region of the primer which is complementary to the polymorphism is at or near the 3' end the primer. In one embodiment of this system the polynucleotide the agent will bind to the wild-type sequence but will not act as a primer for a PCR reaction.

The method may be a Restriction Fragment Length Polymorphism (RFLP) based system. This can be used if the presence of the polymorphism in the polynucleotide creates or destroys a restriction site that is recognized by a restriction enzyme. Thus, treatment of a polynucleotide that has such a polymorphism will lead to different products being produced compared to the corresponding wild-type sequence. Thus, the detection of the presence of particular restriction digest products can be used to determine the presence of the polymorphism.

The presence of the polymorphism may be determined based on the change that the presence of the polymorphism makes to the mobility of the polynucleotide or protein during gel electrophoresis. In the case of a polynucleotide single-stranded conformation polymorphism (SSCP) analysis may be used. This technique measures the mobility of the single stranded polynucleotide on a denaturing gel compared to the corresponding wild-type polynucleotide, the detection of a difference in mobility indicating the presence of the polymorphism. Denaturing gradient gel electrophoresis (DGGE) is a similar system where the polynucleotide is electrophoresed through a gel with a denaturing gradient, a difference in mobility compared to the corresponding wild-type polynucleotide indicating the presence of the polymorphism.

The presence of the polymorphism may be determined using a fluorescent dye and quenching agent-based PCR assay such as the TAQMAN™ PCR detection system. In another method of detecting the polymorphism a polynucleotide comprising the polymorphic region is sequenced across the region which contains the polymorphism to determine the presence of the polymorphism.

Various other detection techniques suitable for use in the present methods will be apparent to those conversant with methods of detecting, identifying, and/or distinguishing polymorphisms. Such detection techniques include but are not limited to direct sequencing, use of "molecular beacons" (oligonucleotide probes that fluoresce upon hybridization, useful in real-time fluorescence PCR; see e.g., Marras, et al., *Genet Anal* 14:151 (1999)); electrochemical detection (reduction or oxidation of DNA bases or sugars; see U.S. Pat. No. 5,871,918 to Thorp, et al.); rolling circle amplification (see, e.g., Gusev et al., *Am J Pathol* 159:63 (2001)); Third Wave Technologies (Madison Wis.) INVADER® non-PCR based detection method (see, e.g., Lieder. Advance for Laboratory Managers, 70 (2000))

Accordingly, any suitable detection technique as is known in the art may be utilized in the present methods.

As used herein, "determining" a subject's genotype does not require that a genotyping technique be carried out where a subject has previously been genotyped and the results of the previous genetic test are available; determining a subject's genotype accordingly includes referring to previously completed genetic analyses.

The present invention also provides for a predictive (patient care) test or test kit. Such a test will aid in the therapeutic use of pharmaceutical compounds, including tyrosine kinase inhibitors, such as lapatinib, based on predetermined associations between genotype and/or phenotypic response to the pharmaceutical compound. Such a test may take different formats, including:

(a) a test which analyzes DNA or RNA for the presence of pre-determined alleles and/or polymorphisms. An appropriate test kit may include one or more of the following reagents or instruments: an enzyme able to act on a polynucleotide (typically a polymerase or restriction enzyme), suitable buffers for enzyme reagents, PCR primers which bind to regions flanking the polymorphism, a positive or negative control (or both), and a gel electrophoresis apparatus. The product may utilise one of the chip technologies as described by the state of the art. The test kit would include printed or machine readable instructions setting forth the correlation between the presence of a specific genotype and the likelihood that a subject treated with a specific pharmaceutical compound will experience a hypersensitivity reaction;

(b) a test which analyses materials derived from the subject's body, such as proteins or metabolites, that indicate the presence of a pre-determined polymorphism or allele. An appropriate test kit may comprise a molecule, aptamer, peptide or antibody (including an antibody fragment) that specifically binds to a predetermined polymorphic region (or a specific region flanking the polymorphism). The kit may additionally comprise one or more additional reagents or instruments (as are known in the art). The test kit would also include printed or machine-readable instructions setting forth the correlation between the presence of a specific polymorphism or genotype and the likelihood that a subject treated with a specific synthetic nucleoside analog will experience a hypersensitivity reaction.

Primers, probes, antibodies and other detection reagents specific for detecting HLA-DQA1*0201, HLA-DQB1*0202, HLA-DRB1*0701, HLA-B*4403, TNXB rs12153855 and/or rs17207923 and/or UGT1A1*28 polymorphisms, as well as a kits or packs comprising at least one of these reagents, are also embodiments of the invention.

Suitable biological specimens for testing are those which comprise cells and DNA and include, but are not limited to blood or blood components, dried blood spots, urine, buccal swabs and saliva. Suitable samples for HLA serologic testing are well known in the art.

The present invention also provides use of lapatinib, or a pharmaceutically acceptable salt or composition thereof, for treating a human for cancer, wherein said human does not have one or more allelic polymorphisms selected from the group of: HLA-DQA1*0201, HLA-DQB1*0202, and/or HLA-DRB1*0701. In one aspect the invention provides use of lapatinib, or a pharmaceutically acceptable salt or composition thereof, for the manufacture of a medicament for treating a human for cancer, wherein said human is genotyped for a polymorphism in HLA and administered lapatinib or a or a pharmaceutically acceptable salt or composition thereof, if said human does not have an allelic polymorphisms selected from the group of: IILA-DQA1*0201, IILA-DQB1*0202, and/or IILA-DRB1*0701. The methods of the present invention can be used in the manufacture of kits and medicaments for treatment with lapatinib, or a pharmaceutically acceptable salt or composition thereof. The methods of the present invention are also understood to described various uses of lapatinib, or a pharmaceutically acceptable salt or composition thereof.

Patents and patent applications cited in this specification are herein incorporated by reference in their entirety as if each individual publication or reference were specifically and individually indicated to be incorporated by reference herein as being fully set forth. Any patent application to which this application claims priority is also incorporated by reference herein in its entirety in the manner described above for patents and patent applications.

The invention is further described by the following non-limiting examples.

EXAMPLES

Raw data used for Examples 1A-C below were taken from the same several clinical trial samples. Data were analyzed and results were confirmed through various analysis as shown below. In the following Examples, lapatinib or a pharmaceutically acceptable salt or composition thereof was used. The commercial form of lapatinib (Tykerb/Tyverb) is currently marketed in a ditosylate monohydrate salt form.

Example 1A

Pharmacogenetic Investigation of Lapatinib Associated Hepatobiliary Safety Signals Clinical data and germline DNA collected during the conduct of thirteen randomised, clinical trials evaluating lapatinib for the treatment of AMBC were used in this pharmacogenetic investigation. The clinical trial protocols were reviewed and approved by Independent Ethics Committees or Institutional Review Boards. Patient informed consent for the pharmacogenetic research was obtained in addition to the patient's consent to participate in the clinical studies. A two-stage strategy for exploratory genetic marker association identification, followed by pre-specified marker confirmation, in independent datasets, was used to identify genetic associations with on-treatment ALT elevation case and control subjects. For the exploratory analysis, was pooled from twelve trials evaluating lapatinib as monotherapy or as a component of various chemotherapy combinations. Nine hundred and one of these patients received lapatinib treatment and were available for ALT case and control selection.

Lapatinib treated ALT case and control subjects were selected from the exploratory (n=901) and confirmation (n=374) cohorts. ALT cases were defined as lapatinib treated patients who had a baseline ALT measurement within the normal range (≤1×ULN) and one or more on-treatment ALT measurement >3×ULN during the course of treatment. ALT controls were patients exposed to lapatinib for at least thirteen weeks, who had baseline and all of their on-treatment ALT measurements within the normal range. The exploratory cohort included 37 ALT cases and 286 controls and the confirmation cohort included 24 ALT cases and 154 controls.

Objective

The objective of this confirmatory pharmacogenetic study was to investigate whether the pre-specified genetic variants were associated with the on-treatment ALT and/or TBL elevations observed within the lapatinib ditosylate monohydrate plus letrozole treatment arm.

Using HLA alleles, DILI candidate genes and the Illumina 1M genome-wide assay platform, exploratory analyses identified genetic variants as significantly associated with ALT or TBL elevation. For the ALT phenotype, nominally significant associations were identified for 58 distinct variants and included three Class II HLA alleles (HLA-DRB1*0701, -DQA1*0201, -DQB1*0202) and one Class I HLA allele (HLA-B*4403) and a SNP in TNXB (A-8829G, rs12153855). For the TBL phenotype, a key result was the association of the Gilbert's syndrome variant UGT1A1*28 with TBL elevation. This example summarises the results of a confirmation analysis using clinical and genetic data from a lapatinib ditosylate monohydrate plus letrozole treatment arm. For the confirmation analysis, a single phase III trial evaluating lapatinib plus letrozole versus letrozole alone, as first-line therapy for postmenopausal hormone receptor-positive metastatic breast cancer was used, which became available after the exploratory analysis was completed. Of those patients receiving lapatinib plus letrozole, 374 patients (57%) were consented and available for ALT case and control selection.

Methodology

Statistical analyses used for this investigation indicated the following. The two phenotypes that were evaluated were maximum on-treatment liver chemistry values for ALT and TBL with respect to the upper limit of normal. These phenotypes were evaluated in both case-control and quantitative trait analyses while key associations were examined qualitatively in the combined ALT/TBL cases. ALT and TBL cases were defined as maximum on-treatment elevations of ≥3×ULN and ≥1.5×ULN, respectively, and control subjects were defined as maximum on-treatment ALT or TBL of ≤1×ULN. Additionally, all cases and controls had normal ALT and TBL at baseline (≤1×ULN) and controls experienced at least thirteen weeks on treatment. Approximately 370 patients with an adequate, fully consented DNA sample had available clinical data for these phenotypes.

A total of 1003 confirmation tests were attempted that were specific to previous endpoints (ALT/TBL), subject population (all subjects/European subjects), and analysis methods (QTA or case-control). These attempted confirmation tests comprised of 999 tests from 833 unique SNPs and 4 tests from 4 HLA alleles. Successful genotypes available for analysis were obtained and tests conducted in 719 unique SNPs (860 tests) and all 4 HLA alleles of interest (4 tests).

Results

For ALT, six genetic markers achieved association in confirmation tests at the p<0.01 level. HLA-DQA1*0201 achieved Bonferroni-adjusted confirmation significance ($p=4.6\times10^{-5}$). Additional confirmed association makers with p<0.01 were HLA-DQB1*0202 and HLA-DRB1*0701 (both $p=2\times10^{-4}$), two SNPs in TNXB (rs12153855, $p=2\times10^4$ and rs17207923, $p=7\times10^{-3}$) and one SNP in HNF1A (rs1169288, $p=7\times10^{-3}$). Although not achieving significance at p<0.01, the next most significant result was HLA-B*4403 (p=0.013). The HLA alleles and TNXB SNPs are located in the same chromosome 6 MHC region and likely reflect a high degree of correlation, suggestive of a single signal. This hypothesis is supported by a conditional analysis for HLA-DQA1*0201, with the five other associated genetic markers becoming non-significant (p>0.05) after adjustment for HLA-DQA1*0201 in the model. HNF1A is located in chromosome 12 and is not correlated with the other top signals. For HLA-DQA1*0201, 17/24 (71%) of ALT cases compared to 32/154 (21%) of controls carried at least one *0201 allele and produced an odds ratio of 9.26 (exact 95% confidence interval 3.26-28.34) when classifying those carrying one or two copies of *0201 allele as the risk group. As a predictive marker of ALT elevation between cases and all non-case subjects, HLA-DQA1*0201 had PPV 0.18 and NPV 0.97 (exact 95% confidence intervals are 0.11-0.27 and 0.95-0.99, respectively).

For TBL, 21 markers achieved confirmed association at p<0.01, however none achieved a Bonferroni-adjusted level of significance. Eighteen of these variants are located in the UGT1 locus. The Gilbert's syndrome UGT1A1 TA7 repeat polymorphism marker (UGT1A1*28) did not show significant association with TBL when evaluated using all genotypes detected as separate classes in the genotypic model (TA5/TA5, TA5/TA6, TA6/TA6, TA6/TA7, TA7/TA7 and TA7/TA8). However significance (p<0.01) was achieved for the highly correlated UGT1A1 SNP (rs887829) and also when TA repeat polymorphism was evaluated for the three common TA repeat genotypes (TA6/TA6, TA6/TA7 and TA7/TA7) only, removing four subjects from the analysis who carried the other three rare genotype classes. Seven of 21 (33%) TBL cases compared to 9/226 (4%) controls carried the TA7/TA7 genotype. An odds ratio of 12.06 (exact 95% confidence interval 3.23-42.16) is achieved when classifying those carrying two copies of TA7 alleles as the risk group. UGT1A1*28 was significantly associated with both baseline TBL and log 10 maximum TBL across all subjects. Overall, these data remain consistent with a UGT1A1*28 Gilbert's syndrome effect on TBL.

For combined ALT/TBL cases with restricted baseline (ALT and TBL values ≤1×ULN at baseline), 6/6 were HLA-DQA1*0201 and -DRB1*0701 allele carriers and 5/6 carried HLA-DQB1*0202. The UGT1A1 TA7/TA7 genotype was carried by 1/6. For combined ALT/TBL cases with unrestricted baseline (ALT and/or TBL values >1×ULN at baseline), 4/6 carried the UGT1A1 TA7/TA7 genotype and 1/6 was a carrier of HLA-DQA1*0201, -DQB1*0202 and -DRB1*0701 alleles.

Conclusions

Using the lapatinib ditosylate monohydrate plus letrozole treatment arm from EGF30008, analyses confirmed the pre-specified genetic markers for ALT elevation: HLA-DQA1*0201/-DQB1*0202/-DRB1*0701. Although not statistically confirmed at a Bonferroni-adjusted level of significance, the UGT1A1*28 association with isolated TBL elevation in this analysis is consistent with a Gilbert's syndrome effect.

Example 1B

Results of Exploratory Pharmacogenetic Investigation of Lapatinib Associated Hepatobiliary Safety Signals Using Candidate Gene Methods Introduction Isolated elevations in serum alanine aminotransferase (ALT) and total bilirubin (TBL) elevations have been observed in patients receiving lapatinib across clinical studies. This exploratory pharmacogenetic study investigated the association of candidate gene polymorphisms with ALT and TBL elevation endpoints. This study utilized patients exposed to lapatinib ditosylate monohydrate (either as monotherapy or in combinations with other therapies) with available clinical data and an adequate, fully consented DNA sample available from twelve lapatinib ditosylate monohydrate advanced and metastatic breast cancer clinical trials.

Objective

The objective of this exploratory pharmacogenetic study was to investigate whether the selected genetic variants were associated with the on-treatment ALT and TBL elevations observed within these studies.

Methodology

Statistical analyses used for this investigation indicated the following. The two phenotypes that were evaluated were maximum on-treatment liver chemistry values for ALT and TBL with respect to the upper limit of normal. These phenotypes were evaluated separately in case-control and quantitative trait analyses and jointly in a combined case-control analysis. ALT and TBL cases were defined as maximum on-treatment elevations of ≥3×ULN and ≥1.5×ULN, respectively, and control subjects were defined as maximum on-treatment ALT or TBL of ≤1×ULN. Approximately 950 patients with an adequate, fully consented DNA sample had available clinical data for these phenotypes. After subject genotyping quality control was completed, a total of 947 patients remained for pharmacogenetic analyses on at least one genetic variant. Due to difference in the incidence of ALT elevations when compared with other treatments, lapatinib ditosylate monohydrate—pazopanib combination-treated patients from VEG20007 were excluded from this primary analysis.

A candidate gene approach of approximately 300 genes was utilized, which included the following: 1) Twenty five genes, selected based lapatinib mechanism pathway and ADME: (CYP, UGT and drug transporter) genes. 2) As genetic understanding of drug-induced liver injury is limited, a comprehensive drug induced liver injury (DILI) panel, developed by GSI in consultation with external liver experts was also evaluated. This DILI panel is comprised of approximately 6500 single nucleotide polymorphisms (SNPs) in 270 gene regions derived from the postulated mechanisms involved in the pathophysiology of DILI. In both approaches, genetic variation in each gene region was investigated using tag SNPs selected from the International HapMap project and/or high density SNP coverage consisting of all functional SNPs with a previously recorded genotype to phenotype correlation. 3) HLA genes (4-digit genotypes of HLA-A, -B, -C, -DPB1, -DQA, -DQB1, and -DRB1, 2-digit genotypes of -DRB3, -DRB4 and -DRB5) were also evaluated since published examples have implicated an immune component in liver injury caused by other drugs. Evaluation of HLA genes focused on a subset of the total number of patients consisting of all ALT cases (N=47) and matched controls (N=47).

Results

For the TBL phenotype, 125 variants from 66 gene regions were significantly (p<0.01) associated with TBL elevation by QTA (N-900) and/or case-control analyses (~60 cases and ~395 controls). Thirty-one of these variants were from one gene region, the UGT1A@ cluster. A key result was the association of the Gilbert's syndrome variant UGT1A1*28 with TBL elevation, significant for both QTA (1.25×10-5, n=899) and case (N=60) and control (N=396) analysis (p=1.04×10-5). Thirty five percent of TBL cases were TA7/TA7 genotype and 82% of TBL cases had at least one TA7 allele, compared to 5% and 48% respectively for controls. Patients homozygous for the UGT1A1*28 variant had an odds ratio (95% CI) of 10.7 (5.3-21.6) of being a case than a control, when compared to the other genotypes.

For the ALT phenotype, 51 variants from 34 gene regions were significantly (p<0.01) associated with ALT elevation by QTA (n-900) and/or case-control analyses (~35 cases and ~285 controls). In the HLA analysis, two genetic signals were significantly associated (p<0.05) with ALT elevation in matched case-control analysis (47 cases and 47 controls): HLA-DRB1*0701 (along with other HLA variants correlated with this allele) and HLA-B*4403. HLA-DRB1*0701 was significantly associated with ALT elevation (p=0.014), with an odds ratio (95% CI) of 4.4 (1.6-12.0) for HLA-DRB1*0701 carriage compared to all other observed HLA-DRB1 alleles. One ALT case had the HLA-DRB1*0701/*0701 genotype and 40% of ALT cases had at least one copy of the IILA-DRB1*0701 allele, compared to none and 13% respectively for controls. HLA-B*4403 was significantly associated with ALT elevation (p=0.033), with an odds ratio (95% CI) of 4.0 (1.1-14.3) for HLA-B*4403 carriage compared to all other observed IILA-B alleles. Twenty three percent of ALT cases carried one copy of the HLA-B*4403 allele (no subjects were observed to carry two copies), compared to 6% respectively for controls.

For combined ALT and TBL cases, 20 variants from 15 gene regions were significantly (p<0.01) associated the combined case-control endpoint (~9 cases and ~225 controls). For key markers, 5/13 combined ALT/TBL cases were UGT1A1*28 TA7/TA7 homozygotes (38%) and 4/13 combined ALT/TBL cases had at least one of the significant HLA alleles discussed above (31%).

Example 1C

Two-Stage Analysis for Exploratory Marker Association Identification, Followed by Pre-Specified Marker Confirmation in Independent Datasets Using ALT Case-Control Analysis Background: Lapatinib is a HER2/EGFR tyrosine kinase inhibitor approved for the treatment of HER2 over-expressing advanced or metastatic breast cancer (AMBC). Serious hepatobiliary adverse events have been observed in a small proportion of lapatinib treated AMBC patients. A two-stage pharmacogenetic investigation of ALT elevation was conducted in AMBC clinical trial patients treated with lapatinib. Methods: Exploratory marker identification evaluated HLA (10 genes), candidate genes (299 genes, 7426 SNPs) and genome wide screening (1M SNPs) in 37 cases with ALT >3× upper limit of normal (ULN) and 286 controls with ALT ≤1×ULN. Markers that achieved pre-specified association thresholds were progressed to an independent confirmatory dataset of 24 ALT cases and 155 controls.
Results: Out of 58 variants associated with >3×ULN ALT elevation in the exploratory dataset, four exceeded the pre-specified significance threshold in the confirmatory analysis. These variants reside in the same MHC genomic locus and include HLA-DQA1*0201, which achieved multiple test corrected significance. In the confirmatory study, DQA1*0201 allele carriage was present in 71% of ALT cases compared to 21% of controls, with an odds ratio of 9.0 (3.2-27.4). As a predictor of liver safety risk (ALT cases versus non-cases), DQA1*0201 had negative and positive predictive values of 0.97 (0.95-0.99) and 0.17 (0.10-0.26), respectively.
Conclusions: These results support a role for immune mechanisms in the hepatotoxicity caused by lapatinib. A test based on DQA1*0201 allele carriage may mitigate liver safety risk during lapatinib treatment in women with AMBC.

Introduction

Lapatinib (Tykerb®/Tyverb®) is a dual HER2/ErbB2 and EGFR/ErbB1 tyrosine kinase inhibitor approved for oral use in combination with capecitabine for the treatment of patients with advanced or metastatic breast cancer (AMBC) whose tumours over-express HER2/ErbB2 and who have received previous therapy including an anthracycline, a taxane and trastuzumab (Finn R S, et al. *J Clin Oncol* 2009; 27: 3908-3915). Lapatinib is also active as a single agent and in combination with other chemotherapy and hormonal agents in patients with HER2/ErbB2 positive metastatic breast cancer (Di Leo, A., et al. *J Clin Oncol*, 2008; 26, 5544-5552 and Johnston S, et al. *J Clin Oncol* 2009; 27; 5538-5546) and inflammatory breast cancer (Christofanilli M, et al, *Breast Cancer Res Treat* 2006; 100: 5S). In addition, large clinical trials are ongoing to evaluate lapatinib monotherapy in the earlier stage of adjuvant breast cancer (Moy B and Goss P E. *Clin Breast Cancer* 2007; 7: 489-492). Extensive clinical experience with lapatinib has demonstrated an acceptable safety profile in the breast cancer therapy setting (Di Leo, A., et al. *J Clin Oncol,* 2008; 26, 5544-5552, and Geyer, C E, et al. *N Engl J Med* 2006; 355: 2733-2743). However, isolated elevations in serum transaminases (including alanine aminotransferase, ALT) and total bilirubin (TBL) have been observed and serious laboratory abnormalities of Grade 3 ALT elevation (Common Toxicity Criteria for Adverse Events, v4.0) and Hy's Rule events have been reported in 1.6% in 0.2% of cancer patients receiving lapatinib (Moy, B, et al. *J Clin Oncology* 2009; 27, 15S (Suppl A1043)). Elevations in serum transaminases and TBL and isolated events of hepatotoxicity have been reported for other tyrosine kinase inhibitors (Loriot Y, et al. *Nature Clinical Practice Oncology* (2008)).

Liver chemistry abnormalities are considered safety signals for liver injury (Mann, R and Andrews, E, (eds), Pharmacovigilance (Wiley and Sons Ltd, Chichester), 2006) and can lead to treatment discontinuation, with subsequent poor disease control in cancer patients. Improved understanding of hepatotoxicity mechanisms may enable better interpretation and management of patients who exhibit these signals. Recent studies have identified strong associations between specific Human Leukocytic Antigen (HLA) polymorphisms within the Major Histocompatibility Complex (MHC) and hepatotoxicity for diverse treatments with unrelated indications. These include amoxicillin-clavulanate (HLA-DRB1*1501, O'Donohue, J, et al. *Gut* 2000; 47: 717-720), anti-tuberculosis chemotherapy (HLA-DQB1*0201, Sharma, S K, et al. *Am J Resp Crit Care* 2002; 166: 916-919), ticlopidine (HLA-A*3303, Hirata K, et al. *The Pharmacogenomics Journal* 2008; 8: 29-33), ximelagatran (HLA-DRB1*0701, Kindmark, A., et al. *Pharmacogenomics Journal,* 2007; 1-10), flucloxacillin (HLA-B*5701, Daly A, flucloxacillin, et al. *Nature* Genetics 2009; 41: 816-819) and lumaricoxib (HLA-DRB1*1501, Wright T M. Presented at 9th Annual FDA/PhRMA/AASLD Hepatotoxicity Meeting, March 2009). The prospective collection of germline DNA during lapatinib clinical trials in breast cancer patients enabled the present pharmacogenetic investigation to identify variants that might serve as predictors of patients with high risk of lapatinib associated liver injury.

Methods

Patient and Clinical Trial Characteristics

Clinical data and germline DNA collected during the conduct of thirteen randomised, clinical trials evaluating lapatinib for the treatment of AMBC were used in this pharmacogenetic investigation. The clinical trial protocols were reviewed and approved by Independent Ethics Committees or Institutional Review Boards. Patient informed consent for the pharmacogenetic investigation was obtained in addition to the patient's consent to participate in the clinical studies.

A two-stage strategy for exploratory genetic marker association identification, followed by pre-specified marker confirmation, in independent datasets, was used to identify genetic associations with on-treatment ALT elevation case and control subjects. For the exploratory analysis, clinical data available as of 16 Apr. 2008 was pooled from twelve trials evaluating lapatinib as monotherapy or as a component of various chemotherapy combinations. The combined intent to treat (ITT) population from these studies was 2198 patients and 1336 (61%) gave consent for pharmacogenetic investigation. A total of 901 patients received lapatinib treatment and were available for ALT case and control selection. For the confirmatory analysis, a single phase III trial evaluating lapatinib plus letrozole versus letrozole alone, as first-line therapy for postmenopausal hormone receptor-positive metastatic breast cancer (Johnston S, et al. *J Clin Oncol* 2009; 27; 5538-5546) was used, which became available after the exploratory analysis was completed. This study had an ITT population of 1286 subjects and 772 (60%) gave consent for pharmacogenetic investigation. Of those patients receiving lapatinib plus letrozole, 374 patients (57%) were consented and available for ALT case and control selection. The clinical characteristics of these genetic study subsets are described in Table 1.

TABLE 1

Clinical Characteristics of Exploratory and Confirmatory Pharmacogenetic Populations

|  | Exploratory Study PGx Population | Confirmatory Study PGx Population |
|---|---|---|
| Disease type | Locally advanced and metastatic breast cancer (12 trials) | Postmenopausal hormone receptor-positive metastatic breast cancer (1 trial) |
| Total N (all female) | 901[1] | 374[2] |
| Age (year): Mean (SD) | 52.2 (11.0) | 63.5 (9.9) |
| Ancestry Groups Informed by Clinical and Genetic Data | European (N = 620, 68.8%) | European (N = 301, 80.5%) |
|  | Hispanic (N = 103, 11.4%) | Hispanic (N = 42, 11.2%) |
|  | India-Pakistani (N = 52, 5.8%) | Pakistani (N = 8, 2.1%) |
|  | Tunisian (N = 33, 3.7%) | Black (N = 8, 2.1%) |
|  | Asian (N = 29, 3.2%) | Asian (N = 5, 1.3%) |
|  | Black (N = 21, 2.3%) | Tunisian (N = 3, 0.8%) |
|  | None—Outliers (N = 24, 2.7%) | None—Outliers (N = 5, 1.3%) |
|  | None—Inadequate Genotype Information (N = 19, 2.1%) | None—Inadequate Genotype Information (N = 2, 0.5%) |
| Liver metastasis (N, %) | 343 (38.1%) | 88 (23.5%) |
| Lapatinib Treatments[3] | Monotherapy (N = 363) | Combination: letrozole (N = 374) |
|  | Combination: paclitaxel (N = 218) |  |
|  | Combination: capecitabine (N = 146) |  |
|  | Combination: trastuzumab (N = 146) |  |
|  | Combination: paclitaxel + carboplatin (N = 3) |  |
|  | Combination: paclitaxel + carboplatin + trastuzumab (N = 4) |  |
|  | Combination: paclitaxel + trastuzumab (N = 21) |  |
| Baseline ALT xULN: Mean(SD)/Median | 0.75 (0.76)/0.52 | 0.64 (0.53)/0.49 |

TABLE 1-continued

Clinical Characteristics of Exploratory and Confirmatory Pharmacogenetic Populations

| | Exploratory Study PGx Population | Confirmatory Study PGx Population |
|---|---|---|
| Baseline TBL xULN: Mean(SD)/Median | 0.47 (0.32)/0.40 | 0.45 (0.22)/0.40 |
| Baseline ALP xULN: Mean(SD)/Median | 1.0 (0.91)/0.75 | 0.99 (0.69)/0.81 |
| Maximum on treatment ALT xULN: Mean(SD)/Median | 1.29 (1.96)/0.80 | 1.53 (1.97)/0.91 |
| Maximum on treatment TBL xULN: Mean(SD)/Median | 0.88 (1.08)/0.68 | 0.93 (1.48)/0.76 |
| Maximum on treatment ALP xULN: Mean(SD)/Median | 1.34 (1.40)/0.91 | 1.57 (1.55)/1.08 |
| Maximum on treatment ALT > 3 xULN (N, %) | 66 (7.3%) | 35 (9.4%) |
| Maximum on treatment ALT > 5 xULN (N, %) | 24 (2.7%) | 19 (5.1%) |
| Maximum on treatment ALT > 8 xULN (N, %) | 9 (1.0%) | 9 (2.4%) |

[1]For the exploratory analysis, clinical data available as of 16 Apr. 2008 was pooled from twelve trials.
[2]For the confirmatory analysis, a single phase III trial was used, which became available after the exploratory analysis was completed.
[3]Subjects with pharmacogenetic data from VEG20007 who received a combination of lapatinib plus pazopanib (n = 46) were excluded from this analysis as this combination was found to produce a higher incidence of ALT elevation than other combinations or lapatinib monotherapy. Lapatinib monotherapy treated patients from VEG20007 (n = 44) were included in this analysis and comprise part of the total number of subjects (n = 901).

The overall design of the study is shown in FIG. 1. Lapatinib treated ALT case and control subjects were selected from the exploratory (n=901) and confirmatory (n=374) cohorts. ALT cases were defined as lapatinib treated patients who had a baseline ALT measurement within the normal range (≤1×ULN) and one or more on-treatment ALT measurement >3×ULN during the course of treatment. ALT controls were patients exposed to lapatinib for at least thirteen weeks, who had baseline and all of their on-treatment ALT measurements within the normal range. The exploratory study included 37 ALT cases and 286 controls and the confirmatory study included 24 ALT cases and 154 controls. The clinical characteristics of these case and control subsets are described in Table 2. As a negative control for lapatinib-induced ALT elevation, the letrozole-only treated patients from the confirmatory study were genotyped for the confirmed alleles. Of those patients receiving letrozole alone, 340 patients (55%) were available for ALT case and control selection, providing 11 cases and 159 controls for the non-lapatanib control analysis.

TABLE 2

Demographics of Exploratory and Confirmatory Study Cases and Controls

| | Exploratory Study ALT Cases | Exploratory Study ALT Controls | Confirmatory Study ALT Cases | Confirmatory Study ALT Controls |
|---|---|---|---|---|
| Disease type | Locally advanced and metastatic breast cancer (12 trials) | Locally advanced and metastatic breast cancer (12 trials) | Postmenopausal hormone receptor-positive metastatic breast cancer (1 trial) | Postmenopausal hormone receptor-positive metastatic breast cancer (1 trial) |
| Total N (all female) | 37 | 286 | 24 | 155 |
| Age (year): Mean (SD) | 50.9 (9.9) | 52.8 (10.6) | 65.5 (9.0) | 64.4 (9.7) |
| Ancestry Groups Informed by Clinical and Genetic Data | European (N = 26) Non-European (N = 8) None[1] (N = 3) | European (N = 196) Non-European (N = 79) None[1] (N = 11) | European (N = 21) Non-European (N = 3) None[1] (N = 0) | European (N = 123) Non-European (N = 28) None[1] (N = 4) |
| Lapatinib Treatment | Monotherapy (N = 14) Combination Therapy (N = 23) | Monotherapy (N = 105) Combination Therapy (N = 181) | Combination Therapy (N = 24) | Combination Therapy (N = 155) |
| Baseline ALT xULN: Mean(SD)/Median | 0.51(0.21)/0.49 | 0.43(0.18)/0.40 | 0.45(0.21)/0.41 | 0.43(0.18)/0.40 |
| Maximum on treatment ALT xULN: Mean(SD)/Median | 6.47(6.57)/4.70 | 0.59(0.21)/0.59 | 6.50(3.73)/4.96 | 0.66(0.19)/0.65 |

[1]Outliers or Inadequate Genotype Information

Patient and Clinical Trial Characteristics

Clinical data and germline DNA collected during the conduct of thirteen randomised, double-blind clinical trials evaluating lapatinib for the treatment of AMBC (as shown in Table 3) were used in this pharmacogenetic investigation. The clinical trial protocols were reviewed and approved by Independent Ethics Committees or Institutional Review Boards. Patient informed consent for the pharmacogenetic research was obtained in addition to the patient's consent to participate in the clinical studies.

TABLE 3

Clinical studies used in this pharmacogenetic investigation

| Study/Treatment | Enrolled[1] | PGx consented[1] | Rec'd Lapatinib & w/ valid LFT clinical data & adequate DNA[1] | Analyzable subjects (post QC)[2] |
|---|---|---|---|---|
| Lapatinib + Trastuzumab | 54 | 35 | 27 | 27 |
| Lapatinib + Capecitabine | 408 | 256 | 142 | 142 |
| Lapatinib + Paclitaxel | 49 | 41 | 38 | 36 |
| Lapatinib | 154 | 64 | 46 | 46 |
| Lapatinib + Carboplatin + Paclitaxel with or without Trastuzumab | 13 | 9 | 7 | 7 |
| Lapatinib + Paclitaxel + Trastuzumab | 33 | 21 | 21 | 21 |
| Lapatinib with or without Trastuzumab | 296 | 203 | 185 | 185 |
| Lapatinib | 242 | 147 | 120 | 120 |
| Lapatinib + Paclitaxel | 57 | 43 | 40 | 40 |
| Lapatinib | 138 | 95 | 93 | 91 |
| Lapatinib + Paclitaxel | 580 | 320 | 145 | 142 |
| Lapatinib with or without Pazopanib | 174 | 102 | 90 | 901 |
| | 2198 | 1363 | 954 | 947 |
| Lapatinib plus letrozole versus letrozole | 1286 | 702 | 468 | 371 |

A two-stage strategy for exploratory genetic marker association identification, followed by pre-specified marker confirmation, in independent datasets, was used to identify genetic associations between on-treatment ALT elevation case and control subjects. For the exploratory cohort, data was pooled from twelve trials evaluating lapatinib as monotherapy or as a component of various chemotherapy combinations. The combined intent to treat (ITT) population from these studies was 2198 subjects and 1336 (61%) gave pharmacogenetic consent. Nine hundred and one patients received lapatinib treatment and were available for ALT case and control selection. For the confirmation cohort, a single trial evaluating lapatinib plus letrozole versus letrozole alone, as first-line therapy for postmenopausal hormone receptor-positive metastatic breast cancer (Johnston S., et al. *J Clin Oncol* 2009; 27; 5538-5546) became available after the exploratory analysis was completed. This study had an ITT population of 1286 subjects and 772 (60%) gave pharmacogenetic consent. Of those patients receiving lapatinib plus letrozole 371 patients (57%) were available for ALT case and control selection. The clinical characteristics of these genetic study subsets are described in Table 1 above.

Liver Chemistry Measurements

ALT, TBL and alkaline phosphatase (ALP) measurements were performed by local institutional laboratories. These values were converted to the unit of 'upper limit of normal' (ULN) by dividing the laboratory values with the institutional lab-specific upper limit of normal values.

Genotyping

Germline DNA was extracted from peripheral blood (Qi-Amp DNA Blood Kit, Qiagen, Valencia, Calif.). This study evaluated candidate gene and genome-wide screening, performed in parallel, to detect case-control association signals in the exploratory cohort. Class I and II HLA genes (seven genes to 4-digit and three genes to 2-digit resolution) were typed by Laboratory Corporation of America (Burlington, N.C.) and Histogenetics (Ossining, N.Y.), or at GSK using the LABType® SSO Typing Test (One Lambda, Canoga Park, Calif.). In addition, candidate genes comprising 850 polymorphisms in 29 genes involved in metabolic disposition of lapatinib and the EGFR signal transduction pathway and 6560 SNPs in 270 genes from a bespoke panel of drug induced liver injury (DILI) genes were genotyped (Golden-Gate platform or Infinium iSelect platform, Illumina, San Diego, Calif.). Whole genome screen genotyping on the Illumina Human 1M-Duo platform was also conducted (Expression Analysis, Durham, N.C.).

For quality control, subjects were evaluated individually for performance in each genotyping platform and for gender consistency. Markers in each platform were evaluated for individual performance across all subjects. Genotype data of control samples was compared for concordance with legacy data held in house and/or available in the public domain. Genotypes for duplicate samples were compared and found to be concordant.

Statistical Analysis

For all variants, departure from Hardy-Weinberg equilibrium (HWE) was tested separately in both the exploratory and confirmatory datasets using an exact test in the ethnic group with the largest sample size (European ancestry subjects). None of the confirmed variants departed significantly from HWE in either the exploratory or confirmatory sets.

For the exploratory study, initial analysis of the GWAS was done using logistic regression, carried out in PLINK (Purcell S, et al. *American Journal of Human Genetics* 2007; 81, 559-575) using the genotypic test option when three genotype classes were observed, or the additive test option when only two genotype classes were observed. The markers that passed the initial screen from the GWAS, and the DILI/CG and HLA marker sets were analyzed with a penalized logistic regression method (SAS Institute inc, Cary, N.C., USA), which performs better than standard logistic regression where case control numbers are low (Heine G. A comparative investigation of methods for logistic regression with separated or nearly separated data. Statistics in Medicine 2006; 25: 4216-4226). In addition to the genotype term, all models included baseline ALT xULN, treatment group (for the exploratory study), and a sufficient number of principal components to account for potential confounding by population structure. Principal components were obtained from EIGENSOFT (Patterson N. et al. *PLoS Genetics* 2006; 2: e190), using study subjects and HapMap founders.

Genetic markers selected for confirmatory were required to achieve pre-defined p-value thresholds in the exploratory analysis of $p \leq 0.05$ for HLA markers, $p \leq 0.01$ for candidate gene markers and $p \leq 10-4$ for whole genome screen SNPs. For markers confirmed at $p \leq 0.01$, measures of potential clinical utility were evaluated. An allele or genotype(s) was designated which conferred a higher risk of ALT elevation and this was compared to the non-risk allele(s)/genotype(s) and the odds ratio (OR), positive predictive value (PPV), and negative predictive value (NPV) calculated.

Results

Patient Characteristics

The exploratory and confirmatory genetic study populations were similar for AMBC, but with differences in terms of age, incidence of liver metastases and different treatment regimens (as shown in Tables 1 and 2). The confirmatory study enrolled post-menopausal hormone receptor positive metastatic breast cancer patients, which reflected the older mean age of the patients in this study. Patients with European ancestry were the most predominant groups and baseline and maximum-on-treatment liver function measures were similar in both datasets.

In the exploratory cohort, using all subjects who received lapatinib and had a baseline and at least one maximum-on-treatment ALT measure, a univariate linear regression analysis was performed to identify factors associated with maximum-on-treatment ALT. Baseline ALT was a significant predictor of maximum-on-treatment ALT elevation ($p<0.001$), whereas age, treatment, liver metastases and self-reported ethnicity were not.

Exploratory and Confirmatory Genetic Association Analysis

A total of 58 unique genetic variants met the thresholds for nominal statistical significance with ALT elevation by case-control analyses and were selected for further analysis in the confirmatory study. Four of the 58 pre-selected exploratory markers were found to be significantly associated with ALT elevation in the confirmatory study ($p<0.01$) by case and control analysis. The four confirmed variants reside in the same MHC genomic locus (Table 4) and include HLA-DQA1*0201 DQB1*0202 and DRB1*0701 plus a SNP in TNXB (rs12153855). The most significant association was for HLA-DQA1*0201 ($p=8.0\times10^{-5}$) which exceeds a stringent multiple testing correction in the confirmatory dataset (Bonferroni $0.05/58=8.0\times10^{-4}$). This is considered conservative since some of the confirmatory tests performed are amongst highly correlated markers. The genomic proximity and correlation amongst these polymorphisms are consistent with a single association signal. This was supported by a hierarchical, conditional regression analysis, where after adjustment for either DQA1*0201 or DRB1*0701, the three remaining variants became non-significant ($p>0.05$, see Table 5). Further discussion will focus on DQA1*0201, but the results for DRB1*0701 are similar (see Table 4).

TABLE 5

Conditioning analysis of HLA/MHC markers in the confirmatory study suggests a single association signal

| Conditioning Marker | Test Marker DQA1*0201 | TNXB rs12153855 | DQB1*0202 | DRB1*0701 |
|---|---|---|---|---|
| HLA-DQA1*0201 | 8.0 × 10−5 | 0.07 | >0.10 | >0.10 |
| TNXB rs12153855 | 0.02 | 0.0002 | 0.01 | 0.09 |
| HL4-DQB1*0202 | 0.05 | 0.007 | 0.0003 | >0.10 |
| HLA-DRB1*0701 | >0.10 | 0.05 | >0.10 | 0.0004 |

Genotypic P values given are conditional on the variant in the first column. Single SNP results are along the diagonal in bold.

Further Evaluation of HLA-DQA1*0201

Figure 2:
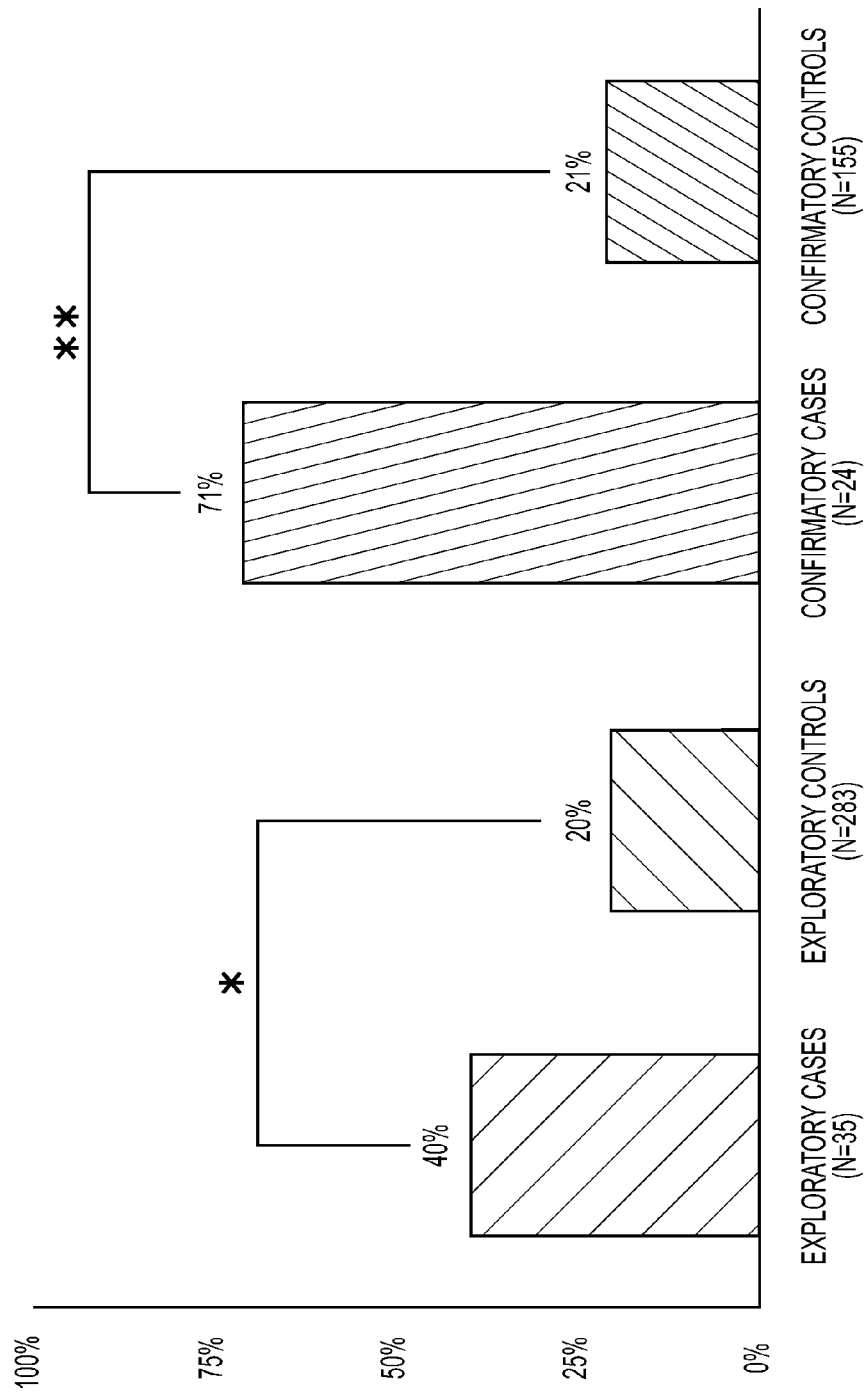
FIG. 2: Proportion of Subjects who Carry HLA-DQA1*0201 by ALT Case-Control Status from Exploratory and Confirmation Cohort.

FIG. 2 compares discrete ALT case-control association data for DQA1*0201. In the exploratory study, 40% (14/35) of cases, compared to 20% (58/283) of controls carried at least one DQA1*0201 allele, whilst in the confirmatory study, 71% (17/24) of cases, compared to 21% (33/155) of controls were DQA1*0201 carriers. When classifying DQA1*0201 allele carriage as the risk group in cases and controls, the exploratory study produced an odds ratio of 2.6 (1.1-5.7), compared to 9.0 (3.2-27.4) in the confirmatory study. Note that the exploratory samples were drawn from twelve studies of different combination therapies; five of the studies were in the refractory treatment setting and were relatively small in sample size, while the confirmatory samples were drawn from a single, large first line treatment study (see Table 1). The stronger association signal in the confirmatory study might therefore be attributed to reduced influence of confounders and less recent prior exposure to chemotherapy.

Figure 3:
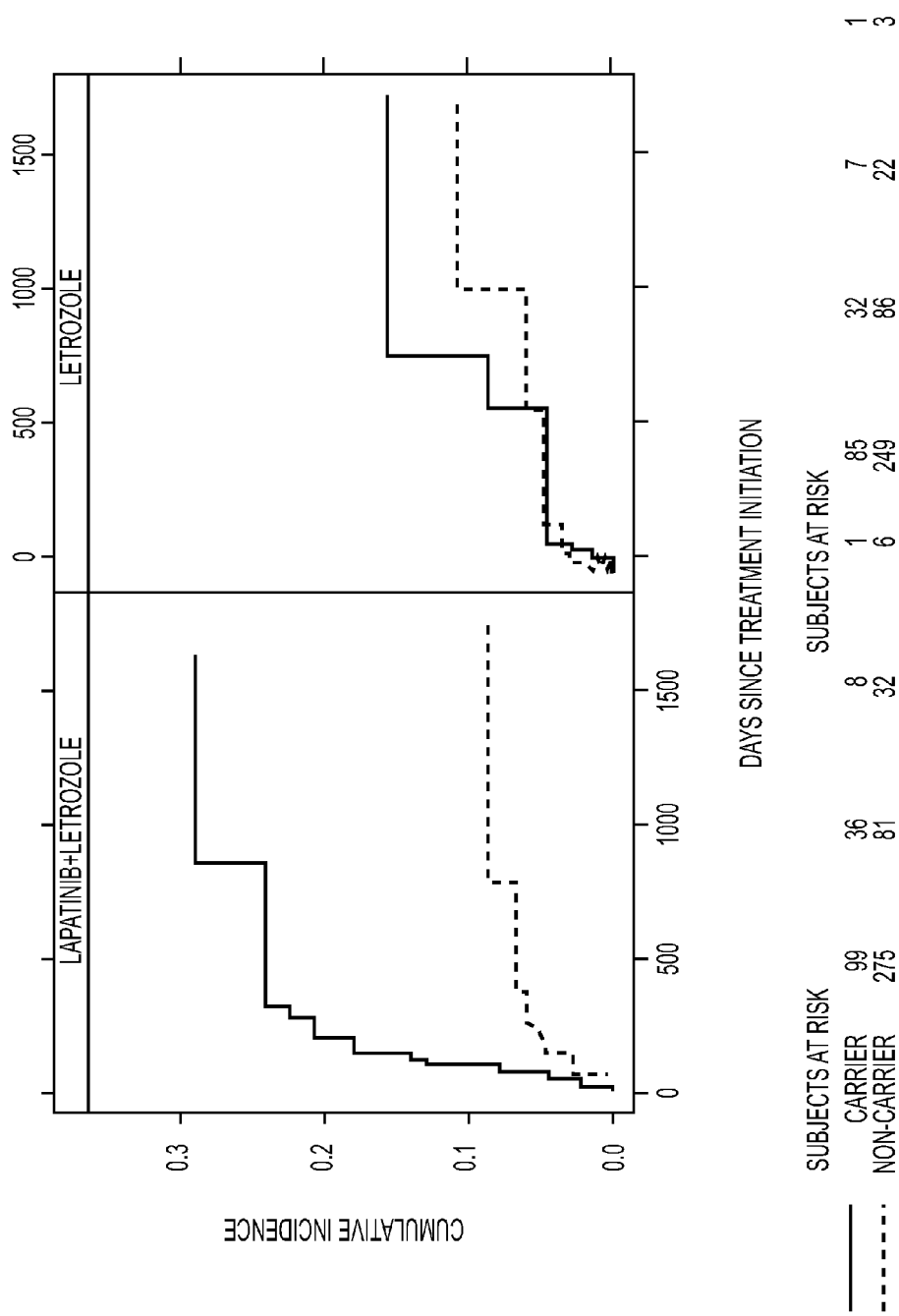
FIG. 3: Cumulative incidence of ALT >3×ULN in lapatinib plus letrozole treatment group HLA-DQA1*0201 carriers and non-carrier subsets, compared with letrozole only treatment group in Confirmation Cohort.

The confirmatory study also offered a means to evaluate the specificity of the lapatanib effect by assessment of the letrozole-only arm in the same trial. In the letrozole-only comparator treatment arm, DQA1*0201 carriage was similar in ALT cases (3/11, 27%) and controls (40/159, 25%). In the confirmatory study, for lapatinib plus letrozole treated patients, FIG. 3 shows DQA1*0201 carriers had a higher cumulative incidence of ALT elevation than non-carriers. In contrast, for the letrozole-only treated patients, the cumulative incidence did not differ between DQA1*0201 carriers and non-carriers. This suggests the DQA1*0201 association was specific for lapatinib induced ALT elevation.

TABLE 4

ALT Case Control analysis of the Four Confirmed, Pre-specified MHC/HLA Region markers

| Variant | Risk allele or genotype | Exploratory study | | | | Confirmatory study | | | |
|---|---|---|---|---|---|---|---|---|---|
| | | Carriage: cases | Carriage: controls | Odds Ratio[1] | P value | Carriage: cases | Carriage: controls | Odds Ratio[1] | P value |
| DQA1 *0201 | *0201[2] | 14/35 (40%) | 58/283 (20%) | 2.6 (1.1, 5.7) | 0.03 | 17/24 (71%) | 33/155 (21%) | 9.0 (3.2, 27.4) | 8.0 × 10−5 |
| TNXB rs12153855 | CC/CT | 12/34 (35%) | 47/281 (17%) | 2.7 (1.1, 6.2) | 0.01 | 15/24 (63%) | 29/155 (19%) | 7.2 (2.6, 20.5) | 0.0002 |
| DQB1 *0202 | *0202[2] | 13/35 (37%) | 47/281 (17%) | 2.9 (1.3, 6.6) | 0.007 | 15/24 (63%) | 30/155 (19%) | 6.9 (2.5, 19.6) | 0.0003 |
| DRB1 *0701 | *0701[2] | 14/35 (40%) | 59/283 (21%) | 2.5 (1.1, 5.6) | 0.04 | 16/24 (67%) | 35/155 (23%) | 6.9 (2.5, 19.9) | 0.0004 |

[1]Case-control odds ratio with exact 95% confidence intervals
[2]Non-risk allele represents all other four-digit alleles observed at the HLA gene of interest As a predictive marker of lapatinib induced ALT elevation (>3×ULN) between cases and all non-case subjects, DQA1*0201 had a high NPV of 0.97 (0.95-0.99), but had a low PPV of 0.17 (0.10-0.26). The DQA1*0201 association and marker performance were maintained for more stringent ALT case thresholds, with higher OR, NPV increasing towards unity, whilst PPV decreased (see Table 6).

TABLE 6

Performance characteristics for HLA-DQA1*0201 carriage and non-carriage with increasing ALT thresholds (>3, 5, 8 xULN) for cases and non-cases in the confirmatory cohort

| | | ALT Cases > 3 xULN | ALT Cases > 5 xULN | ALT Cases > 8 xULN |
|---|---|---|---|---|
| HLA-DQA1*0201 Carrier | Cases | 17 | 9 | 6 |
| | Non Cases | 82 | 90 | 93 |
| HLA-DQA1*0201 Non-Carrier | Cases | 7 | 3 | 1 |
| | Non Cases | 268 | 272 | 274 |
| | OR (CI) | 7.9 (3.0, 23.3) | 9.1 (2.2, 52.8) | 17.7 (2.1, 816) |
| | PPV (CI) | 0.17 (0.10, 0.26) | 0.09 (0.04, 0.17) | 0.06 (0.02, 0.13) |
| | NPV(CI) | 0.97 (0.95, 0.99) | 0.99 (0.97, 0.9977) | 0.9964 (0.98, 0.9999) |

A key liver safety signal is the observation of simultaneous elevations of ALT (≥3×ULN) and TBL (≥2×ULN), combined with no initial findings of cholestasis (ALP <2×ULN), which may reflect extensive hepatocyte damage and impaired hepatic metabolic capacity. Such affected individuals are defined as Hy's Rule cases and carry a high risk of severe liver injury, liver failure and death (Bjornsson E. Clin Pharmac Ther 2006 79: 521-528). Fifteen hepatobiliary adverse event cases (pre-defined in the study protocol as ALT>3× and TBL >1.5×ULN, irrespective of baseline ALT) were identified in the lapatinib plus letrozole arm of the confirmatory study, including two patients adjudicated by liver experts as probable Hy's Rule cases (see Table 7). Eleven of these 15 cases provided DNA, of which, six carried the DQA1*0201 allele (including the one available Hy's Rule case). For the five remaining subjects, who were non-carriers, all had elevated baseline ALT and four had liver metastases prior to treatment.

TABLE 7

Genetic and Clinical Characteristics of pre-defined Hepatobiliary Adverse Events in Confirmatory Study

| Liver AE Category | DNA available | DQA1 *0201 carriage | Elevated Baseline ALT | Liver Metastases at baseline |
|---|---|---|---|---|
| Probable DILI & Hy's | Yes | Yes | No | No |
| | No | Unknown | No | No |
| ALT > 3x | Yes | Yes | No | No |
| TBL > 1.5x | Yes | Yes | No | No |
| ALP < 2x | Yes | Yes | No | Yes |
| | Yes | Yes | No | Yes |
| | No | Unknown | No | No |
| | No | Unknown | No | No |
| ALT > 3x | Yes | Yes | No | Yes |
| TBL > 1.5x | Yes | No | Yes | Yes |
| | Yes | No | Yes | Yes |
| | Yes | No | Yes | Yes |
| | Yes | No | Yes | Yes |
| | Yes | No | Yes | No |
| | No | Unknown | No | No |

These individuals met a pre-defined study protocol definition for hepatobiliary events of ALT > 3x and TBL > 1.5x ULN, irrespective of baseline ALT. In addition two cases were judged as Probable DILI and Hy's Rule cases following adjudication by a liver expert panel.

HLA Class II peptides form heterodimer proteins where DQA1/DQB1 and DRA/DRB1 combinations create discrete antigen binding sites (Jones E Y, et al. Nature Reviews: Immunology 2006; 6; 271-282). HLA-DRA is functionally monomorphic and no further marker discrimination can be gained by evaluating specific allelic combinations. In contrast, both DQA1*0201 and DQB1*0202 are polymorphic. Therefore we investigated alleles that contribute to the DQ2.2 serotype (Fallang, et al, Nature Immunology 2009; 10; 1096-1102), comprising DQA1*0201 as α peptide, with DQB1*0201, *0202 and *0204 (designated as DQB1*0201g) as cis or trans β peptides (Jones E Y, et al. Nature Reviews: Immunology 2006; 6; 271-282) on ALT elevation in the confirmatory study. When compared to DQA1*0201 alone, DQA1*0201/DQB1*0201g allele combinations were maintained in 71% (17/24) of ALT cases but were reduced from 23% (82/350) to 19% (67/348) in the non-cases (see Table 8), resulting in modest improvements in the OR, NPV and PPV.

TABLE 8

Comparison of Performance Characteristics for Carriage of HLA-DQA1*0201 allele Alone versus DQA1*0201/DQB1*0201g allele Combinations (corresponding to DQ2.2 serotype) with ALT Cases (>3x ULN) and Non-cases in the Confirmatory study.

| | | DQA1*0201 ALT Cases > 3 xULN | DQA1*0201/DQB1*0201g ALT Cases > 3 xULN |
|---|---|---|---|
| HLA Carrier | Cases | 17 | 17 |
| | Non Cases | 82 | 67 |
| HLA Non-Carrier | Cases | 7 | 7 |
| | Non Cases | 268 | 281 |
| | OR (CI) | 7.9 (3.0, 23.3) | 10.2 (3.8, 30.0) |
| | PPV (CI) | 0.17 (0.10, 0.26) | 0.20 (0.12, 0.30) |
| | NPV (CI) | 0.975 (0.948, 0.990) | 0.976 (0.951, 0.990) |

Previous reports have suggested different drugs may cause different types of liver injury based on ALT/ALP ratios (Danan G, et al. J Clin Epidemiol 1993; 46: 1323-1330). Amoxicillin and flucloxacillin exhibit cholestatic (O'Donohue, J. et al, Gut 2000; 47: 717-720 and Daly A, et al, Nature Genetics 2009; 41: 816-819) whilst and ximelagatran and lumiracoxib exhibit hepatocellular injury (Kindmark, A, et al. Pharmacogenomics Journal, 2007; 1-10 and Wright T M. MHC II Haplotype marker for lumiracoxib injury. Presented at 9th Annual FDA/PhRMA/AASLD Hepatotoxicity Meeting, March 2009). Lapatinib treated ALT cases demonstrated ratios that were predominantly hepatocellular and mixed rather than cholestatic and DQA1*0201 allele carriage was higher in hepatocellular and mixed, than in the cholestatic injury cases (see Table 9).

TABLE 9

Types of liver injury and HLA-DQA1*0201 status observed in ALT Cases at their time of maximum ALT elevation

| Injury Type | Exploratory Study ALT Cases with HLA Data Available | | Confirmatory Study ALT Cases with HLA Data Available | |
|---|---|---|---|---|
| | N | N that carry DQA1*0201 (%) | N | N that carry DQA1*0201 (%) |
| Cholestatic | 4 | 1 (25%) | 3 | 0 |
| Mixed | 10 | 4 (40%) | 9 | 7 (78%) |
| Hepatocellular | 21 | 9 (43%) | 12 | 10 (83%) |

Liver injury type is based on ALP/ALT ratios determined at time of maximum ALT (22). Low ALP/ALT ratios (R ≤ 2) are defined as cholestatic, high ratios (R ≥ 5) are hepatocellular and ratios between 2 and 5 are considered to have mixed injury.

Discussion

This study has identified and confirmed associations between lapatinib induced ALT elevations and the highly correlated MHC Class II alleles HLA-DQA1*0201, DRB1*0701 and DQB1*0202. The strongest statistical association was observed for DQA1*0201, which has a large genetic effect size consistent with observations in other drug safety studies (Nelson M R, et al. *Pharmacogenomics Journal* 2009; 9 23-33). In the confirmatory study, comparison of DQA1*0201 allele carriage between cases and controls and differences in the cumulative incidence of ALT elevation suggested that removal of DQA1*0201 carriers would reduce the rate of ALT elevation for lapatinib plus letrozole treated patients by more than two-thirds, to a level comparable to letrozole alone treated patients.

The role for HLA alleles in susceptibility to liver safety signals and hepatotoxicity is consistent with previous observations in post-marketing drug use (O'Donohue, J, et al, *Gut* 2000; 47: 717-720 and Daly A, et al, *Nature Genetics* 2009; 41: 816-819) and during clinical trials (Kindmark, A, et al. *Pharmacogenomics Journal*, 2007; 1-10 and Wright TM. MHC II Haplotype marker for lumiracoxib injury. Presented at 9th Annual FDA/PhRMA/AASLD Hepatotoxicity Meeting, March 2009). A previously reported study investigating ximelagatran induced ALT elevation has also identified association of DRB1*0701 and DQA1*02 (Kindmark, A, et al. *Pharmacogenomics Journal*, 2007; 1-10). No consistent pattern in HLA associations has emerged across these different studies, with both Class I and Class II HLA alleles and different MHC haplotypes being implicated. The present findings differ from the previously reported HLA haplotypes for flucloxacillin (Daly A, et al, *Nature Genetics* 2009; 41: 816-819), amoxicillin (O'Donohue, I, et al, *Gut* 2000; 47: 717-720) and lumiracoxib (Wright TM. MHC II Haplotype marker for lumiracoxib injury. Presented at 9th Annual FDA/PhRMA/AASLD Hepatotoxicity Meeting, March 2009). Furthermore, although producing only a modest improvement in marker performance, the association with HLA alleles that form the DQ2.2 serotype favoured a causative role for this specific heterodimer.

HLA associations with lapatinib induced ALT elevation suggest activation of the adaptive immune system to cause a delayed hypersensitivity reaction (Andrade R J, et al. *Hepatology*, 2004; 38, 1603-1612 and Kaplowitz N. *Nature Reviews: Drug Discovery* 2005; 4; 489-499). Drug-induced adaptive immune responses may arise because drugs, or their metabolites, bind covalently to proteins to form haptens, which are recognised by specific HLA proteins and result in T cell driven immune activation and inflammatory tissue damage. A previous report described hepatic microsomal production of a reactive lapatinib metabolite, potentially capable of hapten formation (Zhu Y, Lau Y Y, Djuric S W. In vitro metabolic activation of lapatinib in human and rat liver microsomes. Presented at the 15$^{th}$ North American Meeting of ISSX, Oct. 12-16, 2008). The protein species targeted for lapatinib/metabolite-hapten formation has not been identified, but a candidate would be hepatic CYP3A4, responsible for lapatinib oxidative metabolism (Moy B and Goss P E. *The Oncologist*, 2007; 12: 756-765.). Such a hapten could explain the targeting of the liver, as described previously for CYP2D6 in Type 2 autoimmune hepatitis (Manns et al., *Clin Invest* 1989; 83; 1066-1072 and Lohr I I, et al. *Clin Exp Immunol* 1991; 84: 297-302) and for CYP3A4 in flucloxacillin induced biliary damage (Lakchal F, et al. *Chem Res Toxicol* 2001; 14, 694-701).

The sample size of the exploratory dataset was maximised to increase genetic association signal detection by pooling data from twelve available clinical trials. This approach included patients from multiple studies, geographic locations, different treatment regimens and treatment responsiveness and may include confounding variables that dilute the specific lapatinib genetic signal. It is noteworthy that confirmed genetic associations in this study were obtained from classical HLA and DILI candidate gene selections and not the 1M GWAS, however it is recognised that the large number of SNPs comprising the GWAS necessitated a more stringent significance threshold for exploratory marker selection. Previous studies, with larger case sample sizes and in different disease settings, have successfully utilised GWAS to identify MHC associations with hepatotoxicity and ALT phenotypes (Daly A, et al. *Nature Genetics* 2009; 41: 816-819 and Wright TM. MHC II Haplotype marker for lumiracoxib injury. Presented at 9th Annual FDA/PhRMA/AASLD Hepatotoxicity Meeting, March 2009.)

Retrospective evaluation of ALT elevation in the confirmatory study suggests that testing based on HLA-DQA1*0201 could reduce the incidence of ALT elevation cases to similar to that observed for letrozole treatment alone in AMBC. Determination of patients' DQA1*0201 allele status may also inform options for their clinical management in this challenging disease setting. Whilst demonstrating suitably high negative predictive values for hepatotoxicity risk, application of a test based on DQA1*0201 allele carriage would have a high false positive rate for ALT elevation and hepatotoxicity. This is because the proportion of carriers that develop lapatinib associated liver injury is low compared to study population frequencies of this allele.

Example 2

Methods of Treatment

A patient or a group of patients in need of treatment with lapatinib could receive at least one dose of lapatinib or a pharmaceutically acceptable salt or composition thereof. This dose could be administered either alone or in combination with another drug, including, but not limited to, another anti-cancer agent. Certain liver signals could be tested in each patient both before and after the dosing with lapatinib. Such liver signals could include, but are not limited to, alanine aminotransferase (ALT) and/or total bilirubin (TBL). If ALT and/or TBL and/or other liver signals are found to be elevated in a patient, for instance. ALT is found to be >3.0×ULN, then that patient could be genetically tested for one or more of the following polymorphisms: HLA-DQA1*0201, HLA-DQB1*0202, HLA-DRB1*0701, and/or HLA-B*4403 or other polymorphisms in strong linkage disequilibrium with these. If the patient does not have one or more of these polymorphisms then the patient may receive at least one additional dose of lapatinib.

If the patient does have one or more of these polymorphisms then, subject to clinical judgment, the patient may not receive an additional doses of lapatinib or the patient may remain on lapatinib therapy with further monitoring of liver signals. As is understood in the art, liver signals can be tested periodically through the course of treatment using clinical tested known in the art. Liver tests could occur after each dose or could occur at regular time intervals regardless of when dosing occurs, including, but not limited to, daily, weekly and or monthly. As is also understood in the art, continued treatment with lapatinib is a clinical determination. If a patient shows increased ALT to above 3×ULN and has a polymorphism selected from HLA-DQA1*0201, HLA-DQB1*0202, and/or HLA-DRB1*0701 the patient may be discontinued from lapatinib treatment, alternative therapy may be administered, and/or the dose of lapatinib or a pharmaceutically acceptable salt or composition thereof may be reduced or suspended and then restarted.

The invention claimed is:

1. A method of treating a human for breast cancer comprising:
   (a) obtaining a biological sample from said human;
   (b) detecting whether an allelic polymorphism at HLA-DQA1*0201 is present in said biological sample;
   (c) determining that said human does not have an allelic polymorphism at HLA-DQA1*0201 based on detecting the absence of said allelic polymorphism in step (b); and
   (d) administering at least one dose of lapatinib or a pharmaceutically acceptable salt or composition thereof to said human, thereby treating the human for breast cancer.

2. The method according to claim 1, wherein lapatinib, or a pharmaceutically acceptable salt or composition thereof, is administered to said human as monotherapy.

3. The method according to claim 1, wherein said lapatinib, or a pharmaceutically acceptable salt or composition thereof, is co-administered with at least one other anti-cancer agent.

4. The method according to claim 3, wherein said at least one other anti-cancer agent is selected from the group of: trastuzumab, capecitabine, paclitaxel, carboplatin, pazopanib and letrozole.

5. The method according to claim 1, further comprising determining that said human is not DQ2.2. seropositive where DQ2.2 is not detected to be present in said human.

6. The method according to claim 1, wherein said human does not show significant elevation in alanine aminotransferase (ALT) and/or total bilirubin (TBL) after the administration of at least one dose of lapatinib, or a pharmaceutically acceptable salt or composition thereof.

* * * * *